US012367946B2

(12) United States Patent
Tran

(10) Patent No.: US 12,367,946 B2
(45) Date of Patent: *Jul. 22, 2025

(54) PERSONALIZED HEALTH OR BEAUTY SYSTEM

(71) Applicant: Ha Tran, Saratoga, CA (US)

(72) Inventor: Ha Tran, Saratoga, CA (US)

(73) Assignee: Bao Tran, Saragota, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 18/135,094

(22) Filed: Apr. 14, 2023

(65) Prior Publication Data

US 2023/0253069 A1    Aug. 10, 2023

Related U.S. Application Data

(63) Continuation of application No. 16/866,922, filed on May 5, 2020, now Pat. No. 11,657,896, which is a (Continued)

(51) Int. Cl.
| | | |
|---|---|---|
| *G01N 33/48* | (2006.01) |
| *C12Q 1/6869* | (2018.01) |
| *C12Q 1/6876* | (2018.01) |
| *G01N 33/50* | (2006.01) |
| *G06N 5/04* | (2023.01) |

(Continued)

(52) U.S. Cl.
CPC .......... *G16B 20/00* (2019.02); *C12Q 1/6869* (2013.01); *C12Q 1/6876* (2013.01); *G06N 5/04* (2013.01); *G06N 7/01* (2023.01); *G06N 20/00* (2019.01); *G16B 40/00* (2019.02)

(58) Field of Classification Search
CPC ........ G16B 20/00; G16B 40/00; G16B 20/10; G16B 20/20; G16B 40/20; G16B 40/30; C12Q 1/6869; C12Q 1/6876; G06N 5/04; G06N 7/01; G06N 20/00; G06N 3/045; G06N 3/08
See application file for complete search history.

(56) References Cited

U.S. PATENT DOCUMENTS 10,381,105 B1 * 8/2019 Tran .................. G06N 5/04
10,685,739 B2 * 6/2020 Tran .................. C12Q 1/6869
(Continued)

FOREIGN PATENT DOCUMENTS

WO     WO-02090583 A2 *  11/2002  ........ A61K 38/1709
WO     WO-2016138337 A1 *  9/2016  .......... C12Q 1/6806

OTHER PUBLICATIONS

Liang et al. Hierarchical Bayesian Neural Network for Gene Expression Temporal Patterns, Stat Appl Genet Mol Biol, Sep. 3, 2004, pp. 1-24. (Year: 2004).*

*Primary Examiner* — Russell S Negin
(74) *Attorney, Agent, or Firm* — PatentPC

(57) ABSTRACT

Systems and methods disclosed for recommending healthy actions for a subject by using a DNA sequencer to generate genetic information; aggregating genetic information, health or beauty trend data, and health response from a patient population; deep learning with a computer to generate at least one computer implemented classifier that predicts matching health protocols, treatment regimes, or products based on the genetic information, health trend data, and health product response from a patient population; and recommending one or more actions, protocols, or products, for the subject.

19 Claims, 9 Drawing Sheets

Related U.S. Application Data continuation of application No. 16/455,310, filed on Jun. 27, 2019, now Pat. No. 10,685,739, which is a continuation of application No. 15/414,563, filed on Jan. 24, 2017, now Pat. No. 10,381,105.

(51) Int. Cl.
*G06N 7/01* (2023.01)
*G06N 20/00* (2019.01)
*G16B 20/00* (2019.01)
*G16B 40/00* (2019.01)

(56) References Cited

U.S. PATENT DOCUMENTS

| | | | |
|---|---|---|---|
| 11,657,896 B2 * | 5/2023 | Tran | G16B 20/10 703/11 |
| 2005/0221334 A1 * | 10/2005 | Benson | G01N 33/6881 435/6.14 |
| 2006/0216237 A1 * | 9/2006 | Brooks | A61K 47/642 424/1.69 |
| 2010/0216891 A1 * | 8/2010 | Shimono | A61P 9/12 514/675 |
| 2011/0044993 A1 * | 2/2011 | Kronthaler | C07K 16/2803 436/63 |
| 2013/0183673 A1 * | 7/2013 | Nistico | C07K 14/435 435/7.1 |
| 2022/0002809 A1 * | 1/2022 | Horvath | C12Q 1/6883 |

* cited by examiner

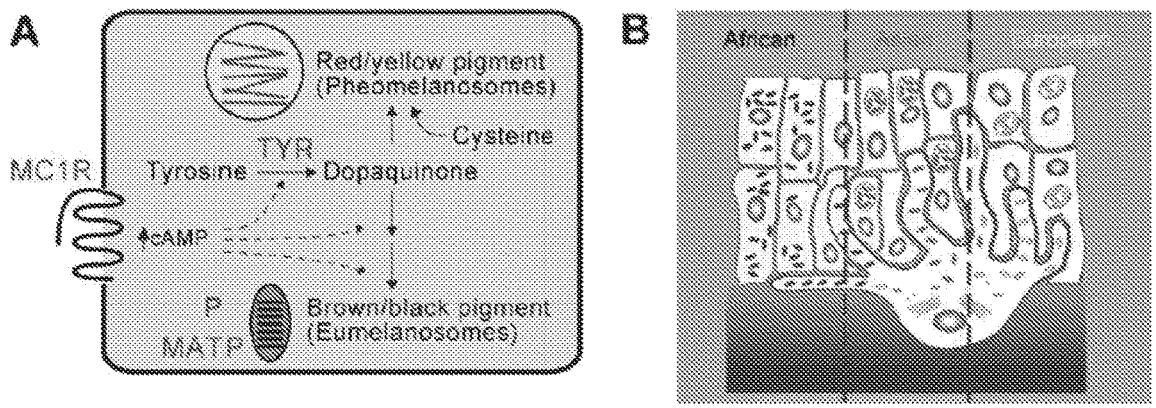

FIG. 1A

| |
|---|
| 110 – capture facial image or video |
| 120 - identify visual skin tone from the image |
| 130 – capture swipe of patient DNA |
| 140 – process DNA for user markers of interest relating to skin, for example |
| 150 - retrieve cosmetic material data and cosmetic material interaction data for each of the imaged substances and determine relative interactions between substances |
| 160 - measure attributes of the cosmetic products and store in database |
| 170 – apply pharmacogenomic information to the cosmetic material-cosmetic material interaction data |
| 180 – identify beauty products recommended based on attributes of the cosmetic products and select the best matching cosmetic product or health product |
| 190 – render DNA based beauty product recommendation and/or health recommendation (such as cancer risk) in a report such as a paper report or a graphical user interface display |

FIG. 1B

| |
|---|
| 310 - construct a comprehensive gene-cosmetic material-cosmetic material interactions (GDDIs) training dataset that includes all pharmaceutical, pharmacokinetic (PK), pharmacogenetic (PG), and pharmacodynamic (PD) GDDIs from multiple data sources for each cosmetic material in a set of cosmetic materials used by a plurality of subjects |
| 320 - construct side effect features for each of the cosmetic materials in the set from genetic panels for an individual and side effects associated with the cosmetic materials in the set |
| 330 - build, using the GDDIs training dataset, a GDDIs classifier for predicting whether or not a given cosmetic material pair derived from the set of cosmetic materials results in adverse interactions, and repeat this process for all possible cosmetic material pairs derivable from the set of cosmetic materials |
| 340 - obtain predicted GDDIs a trained classifier such as a deep learning machine (FIG. 4) |
| 350 - for each side effect, build data structure with side effect features and perform test to determine whether that side effect is differentially shown between positive predicted GDDIs and negative predicted GDDIs |
| 380 -- determine relative interactions between the different cosmetic material substances by locating references in the interaction data for each of the cosmetic material substances to others of the substances |
| 390 render the relative interactions within a report such as a paper report or a graphical user interface display |

FIG. 3

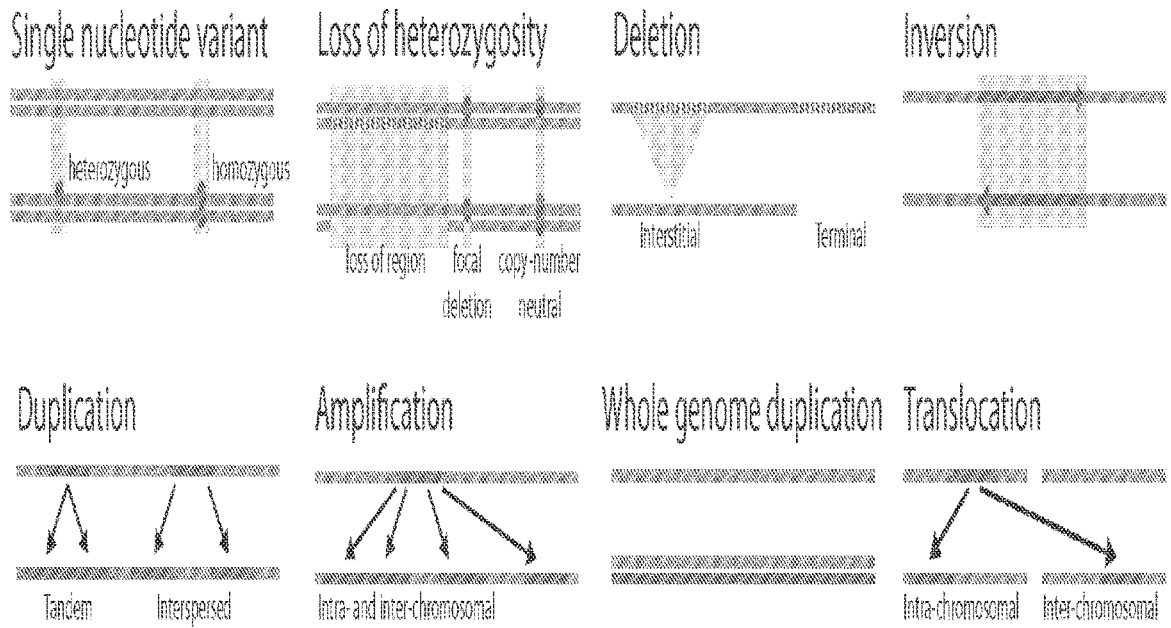
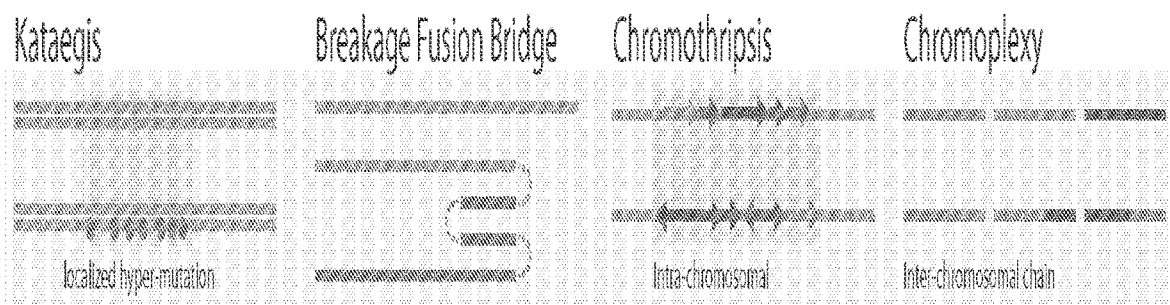
FIG. 5A

PERSONALIZED HEALTH OR BEAUTY SYSTEM

BACKGROUND

The present invention relates to the field of genetic based beauty/healthcare product selection.

Existing beauty products are not optimized for each person. For example, in improving beauty, proper skin tone determination is key. The skin's undertone is the warm, cool, or neutral hue that shows through the surface color of skin. Although the surface color of skin changes depending on sun exposure and other skin conditions like rosacea and acne, the skin's undertone remains consistent. The undertone is warm, cool or neutral is the key to ensuring that your foundation matches skin and that other makeup products apply to look natural. When foundation doesn't properly match skin's undertone, the color stands out as orange to copper, pink to rose, or ashen. In addition to beauty applications, the skin color is also needed in protecting against skin cancer.

SUMMARY

In one aspect, systems methods disclosed for recommending health/beauty products for a subject by using a genetic machine such as spectrophotometer or a DNA sequencer to generate genetic information; aggregating genetic information, and cosmetic product response from a patient population; deep learning with a computer to generate at least one computer implemented classifier that predicts matching beauty products based on the genetic information, beauty trend data, and cosmetic product response from a patient population; and recommending one or more beauty products for the subject.

In another aspect, a system includes a cosmetic or health additive substance to be consumed by a subject and one or more indicia labeling the substance with: genomic biomarkers; material exposure and clinical response variability; risk for adverse events; genotype-specific dosing; polymorphic cosmetic material target and disposition genes; and treatment based on the biomarker.

Advantages of the system may include one or more of the following. The systems and methods use DNA markers together with proprietary DNA Database and algorithm for personalized cosmetic matching by defining a person's skin traits. The systems-based approach combines the interaction of markers in specific genes directly affecting skin pigmentation together with global population markers and accounts for epistatic gene-gene as well as gene-by-environment interactions. The system provides a comprehensive spectrum of variation in skin color genetic markers and corresponding highly specific skin color shades to enhance beauty for women. Additionally, the system can avoid allergic reactions. It can also recommend perfumes based on DNA. This will lower the costs that come about due to adverse cosmetic material side effects and prescription of cosmetic materials that have been proven ineffective in certain genotypes. Cosmetic material companies can develop and license a cosmetic material specifically intended for those who are the small population genetically at risk for adverse side effects.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 1A shows exemplary DNA and skin tone illustrations;

FIG. 1B show exemplary cosmetic DNA mapping and cosmetic recommendation process;

FIG. 3 is a flow chart illustrating a process for pharmacogenetics cosmetic material interaction information retrieval;

FIG. 5A shows various common aberrations in cancer genomes;

DETAILED DESCRIPTION OF THE INVENTION

Figure 1C:
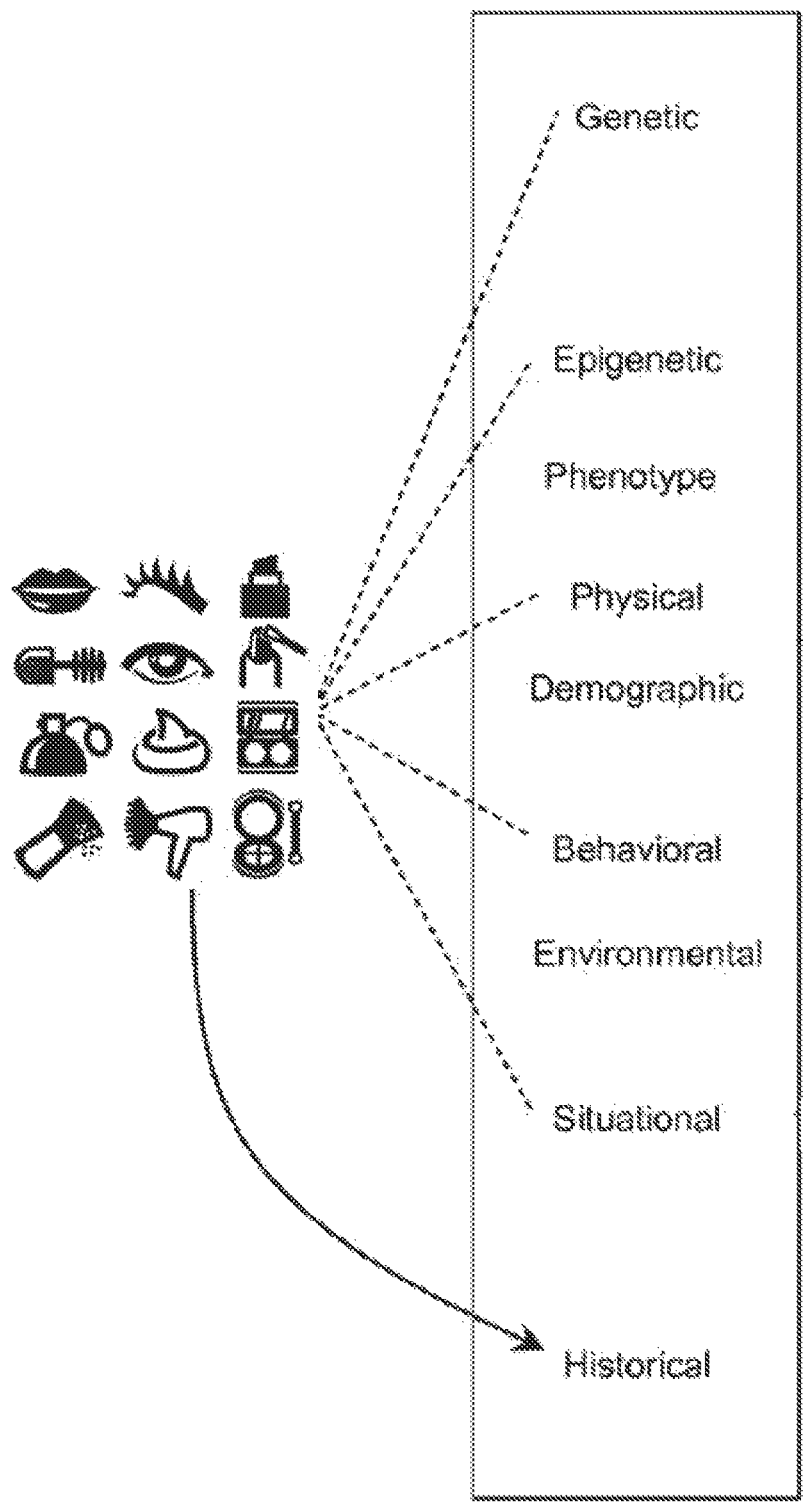
FIG. 1C shows an exemplary system to collect lifestyle and genetic data from various populations for subsequent cosmetic prediction and recommendation to similarly situated users.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers. Inc., 1995 (ISBN 1-56081-569-8). As used herein and in the appended claims, the singular forms "a", "an", and "the" include plural referents unless the context clearly dictates otherwise. Unless defined otherwise, all technical and scientific terms used herein have the same meaning as commonly understood to one of ordinary skill in the art to which this disclosure belongs. "Comprising" means "including." All publications, patent applications, patents, and other references mentioned herein are incorporated by reference in their entirety.

Embodiments of the present invention provide a method, system and computer program product for computer identification (scanning or imaging of cosmetic materials) for cosmetic material interaction information retrieval. In accordance with an embodiment of the present invention, multiple different cosmetic materials can be scanned or imaged to detect identifiable content disposed on the different cosmetic materials. Each cosmetic material can be compared to a data store of cosmetic material information to identify each cosmetic material. Thereafter, pharmacogenetics data and cosmetic material interaction data can be retrieved for each identified cosmetic material. Further, known cosmetic material-cosmetic material interactions and genetic impacts for the identified cosmetic materials can be determined and a report can be provided to include the known cosmetic material-cosmetic material interactions. In this way, precision medicine and cosmetic material-cosmetic material interactions resulting from the use of the multiple different cosmetic materials can be determined without recourse to a voluminous text of cosmetic material interactions.

FIG. 1B show an exemplary process for computer detection of substances or cosmetic materials for cosmetic material interaction information retrieval. Turning now to FIG. 1B, 110 operation includes capture facial image or video. 120 operation is used to identify visual skin tone from the image. In 130 a swipe of patient DNA is captured. In 140 the DNA is processed for user markers of interest relating to skin, for example. In 150 the process retrieves cosmetic material data and cosmetic material interaction data for each of the imaged substances and determines relative interactions between substances. In 160 the process measures attributes of the cosmetic products and store in database. In 170, the process applies pharmacogenomic information to the cosmetic material-cosmetic material interaction data. In 180 the process identifies beauty products and makes recommendations based on attributes of the cosmetic products and selects the best matching cosmetic product or health product. In 190, the process renders DNA based beauty product recommendation and/or health recommendation (such as cancer risk) in a report such as a paper report or a graphical user interface display.

While FIG. 1B discusses capturing cosmetic material interaction, the process can be used to capture environmental factors of FIG. 1A. In yet other embodiments, the process cryptographically reads substance content from RF tag or barcode on a secure cosmetic container bottle and identifies content for the cosmetic substance. Identified substances are added to an interaction list and the process determines if additional substances remain to be scanned (RF/Bar Code) and continues processing. The interaction list now populated by a list of scanned substances is processed. Next, the process retrieves cosmetic material data and cosmetic material interaction data for each of the scanned substances and determines relative interactions between substances. The process receives genetic scans for subjects. The process applies pharmacogenomic information to the cosmetic material-gene interaction data and selects the best medication and identify people who need an unusually high or low dose. Relative interactions can be rendered within a report such as a paper report or a graphical user interface display.

In some examples, one or more pages describing the recommended personalized treatment serums and supplements based on the individuals high and medium risk category results are listed. For example, following recommendations for non-customized products, one or more custom-designed products may be recommended based on the DNA report. These recommendations may include a combination of treatment serums/nutritional products that address the individual strengths and weaknesses of the individuals skin as determined by their DNA report. These customized recommendations many include products such as:

a. Serums:
    1. Vitamin C Treatment Serum
    2. Hyaluronic Moisture Treatment Serum
    3. Wrinkle Treatment Serum
    4. Calming Treatment Serum
  b. Supplements:
    1. Antioxidant Defense
    2. Glycation Defense
    3. Sun Defense
    4. Collagen Defense
    5. Inflammation Defense The determination as to which products will be custom recommended may be based on an algorithmic protocol that matches the ingredients in the products to the weakness that the person's DNA analysis reveals as identified in their medium or high risk categories. This may be programmed based on an algorithm into the computer system that generates the DNA report. High risk categories are an influencing category as recommendations to follow as they provide the individual the greatest opportunity to improve the health and appearance of their skin followed by the medium risk category recommendations. For instance, if a person is determined to be medium or high risk for collagen, products will be recommended that support healthy collagen production and maintenance in the skin. The ingredients in the products that support healthy collagen production and maintenance will be selected and put into the skin care products and nutritional supplements based on clinical research that supports the clinical effectiveness of the ingredients included in the product on the category to which it applies. Raw ingredient selection may be supported by clinical research regarding the effectiveness of the ingredient as identified in both peer-reviewed literature as well as clinical studies. These human clinical studies may be performed by a raw ingredient manufacturer to validate and support the effectiveness of the ingredient in well-controlled human trials. In some examples, product recommendations will be organized into high risk and medium risk categories on the report for ease of understanding and product selection by the individual. In some examples, if a product is already listed under a high-risk category, it will not be relisted under a medium risk category as it is already selected by the algorithm and recommended. In some examples, ingredients will be upgraded and changed on a regular basis based on the current science and literature as new ingredients with better product effectiveness become available in the raw ingredient marketplace.

In some examples, following the formulation process and algorithmic recommendations above, products may be clinically used and evaluated in a clinical practice to ensure that the effectiveness, aesthetic appeal and client satisfaction are of the highest standards possible.

It is contemplated that disclosed products may be distributed into the marketplace through various distribution models which may include direct to consumer, business to business, direct sales through a Multilevel marketing program, television/infomercial. In some examples, after reviewing the report, the report may be provided to the subject, either directly or indirectly (e.g., electronically or standard mail) and an optional customer service meeting/call is set up for those who desire to go over the results and product recommendations, and/or have questions regarding their report In some embodiments, a method of characterizing a subject's skin is provided which includes generating a personalized skin profile. In some examples, generating a personalized skin profile includes determining a subject's genetic potential in at least one area of skin health or appearance by analyzing one or more skin health-associated single nucleotide polymorphisms (SNPs) or other genetic marker associated with the particular area of skin health or appearance being assessed in a biological sample obtained from the subject. In some examples, a subject's genetic potential is determined in one to five or more areas of skin health by analyzing one or more skin health-associated SNPs or other genetic markers associated with the one to five or more areas of skin health in a sample obtained from the subject. The one or more areas of skin health can include assessing the following or more factors: collagen formation, sun protection, antioxidant protection, glycation protection and inflammation control. The generated skin profile reveals the subject's genetic strengths, weaknesses and/or risks related to the one or more areas of skin health thereby allowing a personalized skincare and/or nutritional regimen to be developed and implemented. In some examples, a disclosed method of characterizing a subject's skin further includes identifying SNPs or other genetic markers associated with a particular area of skin health. For example, SNPs associated with a particular area of skin health can be identified by searching the publicly available SNP on the Worldwide Web (see for example, domain name ncbi.nlm.nih.gov/snp; domain name ncbi.nlm.nih.gov/projects/SNP/; or domain name snp.cshl.org/) and determining SNPs associated with particular skin conditions. In some examples, a disclosed method of characterizing a subject's skin further includes providing the results of the characterization study to the subject. In some examples a disclosed method of characterizing a subject's skin further includes recommending and/or providing one or more skincare treatments to the subject based upon the skin profile generated by the characterization analysis. In some examples, the disclosed method of characterizing a subject's skin is performed at home. For example, a subject utilizes a kit designed to allow a subject to generate a skin profile by obtaining a DNA sample at home with the kit which includes an instruction booklet, a questionnaire, a DNA swab, a collection envelope with dessicant to place the specimen in after collection. This sample is then sent for analysis and evaluation and a report is generated for the individual.

In some examples, the kit includes a means for obtaining a biological sample, such a buccal swab and a collection vial which allows the sample to be stored during shipment to the analysis laboratory. The instructions for use can in any form, such as in a pamphlet or provided via electronic means, such as a website on the Worldwide Web.

In some examples, the disclosed method includes identifying one or more, such as one, two, three, four, five or more, categories of skin health and clinical studies to prove these categories have an impact on the skin (glycation causes aging, etc). For example, one or more SNPs is identified by identifying an SNP with an RS number that affects the enzyme or function in each category. Studies, such as clinical studies, are performed to identify the variations of the base at this location to validate that it is an SNP versus an infrequent variant and the clinical significance of this (it affects collagenase, etc.) Tests are then performed to identify which base patterns are protective versus risk promoting. The impact of the one or more SNPs identified on each skincare category is determined, such as by use of an algorithm. Additional studies are then performed to show that the disclosed treatments/protocols impact that area of skin health.

FIG. 1C shows an exemplary system to collect skin color, lifestyle and genetic data from various populations for subsequent prediction and recommendation to similarly situated users. The system collects attributes associated with individuals that co-occur (i.e., co-associate, co-aggregate) with attributes of interest, such as specific disorders, behaviors and traits. The system can identify combinations of attributes that predispose individuals toward having or developing specific disorders, behaviors and traits of interest, determining the level of predisposition of an individual towards such attributes, and revealing which attribute associations can be added or eliminated to effectively modify his or her lifestyle to avoid medical complications. Details captured can be used for improving individualized diagnoses, choosing the most effective therapeutic regimens, making beneficial lifestyle changes that prevent disease and promote health, and reducing associated health care expenditures. It is also desirable to determine those combinations of attributes that promote certain behaviors and traits such as success in sports, music, school, leadership, career and relationships. For example, the system captures information on epigenetic modifications that may be altered due to environmental conditions, life experiences and aging. Along with a collection of diverse nongenetic attributes including physical, behavioral, situational and historical attributes, the system can predict a predisposition of a user toward developing a specific attribute of interest. In addition to genetic and epigenetic attributes, which can be referred to collectively as pangenetic attributes, numerous other attributes likely influence the development of traits and disorders. These other attributes, which can be referred to collectively as non-pangenetic attributes, can be categorized individually as physical, behavioral, or situational attributes.

FIG. 1C displays one embodiment of the attribute categories and their interrelationships according to the present invention and illustrates that physical and behavioral attributes can be collectively equivalent to the broadest classical definition of phenotype, while situational attributes can be equivalent to those typically classified as environmental. In one embodiment, historical attributes can be viewed as a separate category containing a mixture of genetic, epigenetic, physical, behavioral and situational attributes that occurred in the past. Alternatively, historical attributes can be integrated within the genetic, epigenetic, physical, behavioral and situational categories provided they are made readily distinguishable from those attributes that describe the individual's current state. In one embodiment, the historical nature of an attribute is accounted for via a time stamp or other time based marker associated with the attribute. As such, there are no explicit historical attributes, but through use of time stamping, the time associated with the attribute can be used to make a determination as to whether the attribute is occurring in what would be considered the present, or if it has occurred in the past. Traditional demographic factors are typically a small subset of attributes derived from the phenotype and environmental categories and can be therefore represented within the physical, behavioral and situational categories.

An individual possesses many associated attributes which may be collectively referred to as an 'attribute profile' associated with that individual. In one embodiment, an attribute profile can be considered as attributes that are present (i.e., occur) in that profile, as well as being comprised of the various combinations (i.e., combinations and subcombinations) of those attributes. The attribute profile of an individual is preferably provided to embodiments of the present invention as a dataset record whose association with the individual can be indicated by a unique identifier contained in the dataset record. An actual attribute of an individual can be represented by an attribute descriptor in attribute profiles, records, datasets, and databases. Herein, both actual attributes and attribute descriptors may be referred to simply as attributes. In one embodiment, statistical relationships and associations between attribute descriptors are a direct result of relationships and associations between actual attributes of an individual. In the present disclosure, the term 'individual' can refer to a singular group, person, organism, organ, tissue, cell, virus, molecule, thing, entity or state, wherein a state includes but is not limited to a state-of-being, an operational state or a status. Individuals, attribute profiles and attributes can be real and/or measurable, or they may be hypothetical and/or not directly observable.

Since the system captures information from various diverse populations, the data can be mined to discover combinations of attributes regardless of number or type, in a population of any size, that cause predisposition to an attribute of interest. The ability to accurately detect predisposing attribute combinations naturally benefits from being supplied with datasets representing large numbers of individuals and having a large number and variety of attributes for each. Nevertheless, the present invention will function properly with a minimal number of individuals and attributes. One embodiment of the present invention can be used to detect not only attributes that have a direct (causal) effect on an attribute of interest, but also those attributes that do not have a direct effect such as instrumental variables (i.e., correlative attributes), which are attributes that correlate with and can be used to predict predisposition for the attribute of interest but are not causal. For simplicity of terminology, both types of attributes are referred to herein as predisposing attributes, or simply attributes, that contribute toward predisposition toward the attribute of interest, regardless of whether the contribution or correlation is direct or indirect.

The multiplex-SNP-assay consists of a multiplex-PCR that amplifies eight regions. The amplification is checked on the Agilent Bioanalyzer. The PCR products are purified by using the ExoSAP-IT kit to prevent remaining primers or dNTPs from interfering with the following step. The SBPE reaction is performed by using the SNaPshot Multiplex kit. The SBPE product is treated with Shrimp Alkaline Phosphatase to dephosphorylate the fluorescently labeled dNTPs. This prevents further reactions of the dNTPs that could lead to extra-peaks in the electropherogram of the multicolor capillary electrophoresis. The products of the multiplex-SNP-assay are separated by color and size and detected using the 3130×1 multicolor capillary electrophoresis. Data analysis is performed with GeneMapper.

Figure 2:
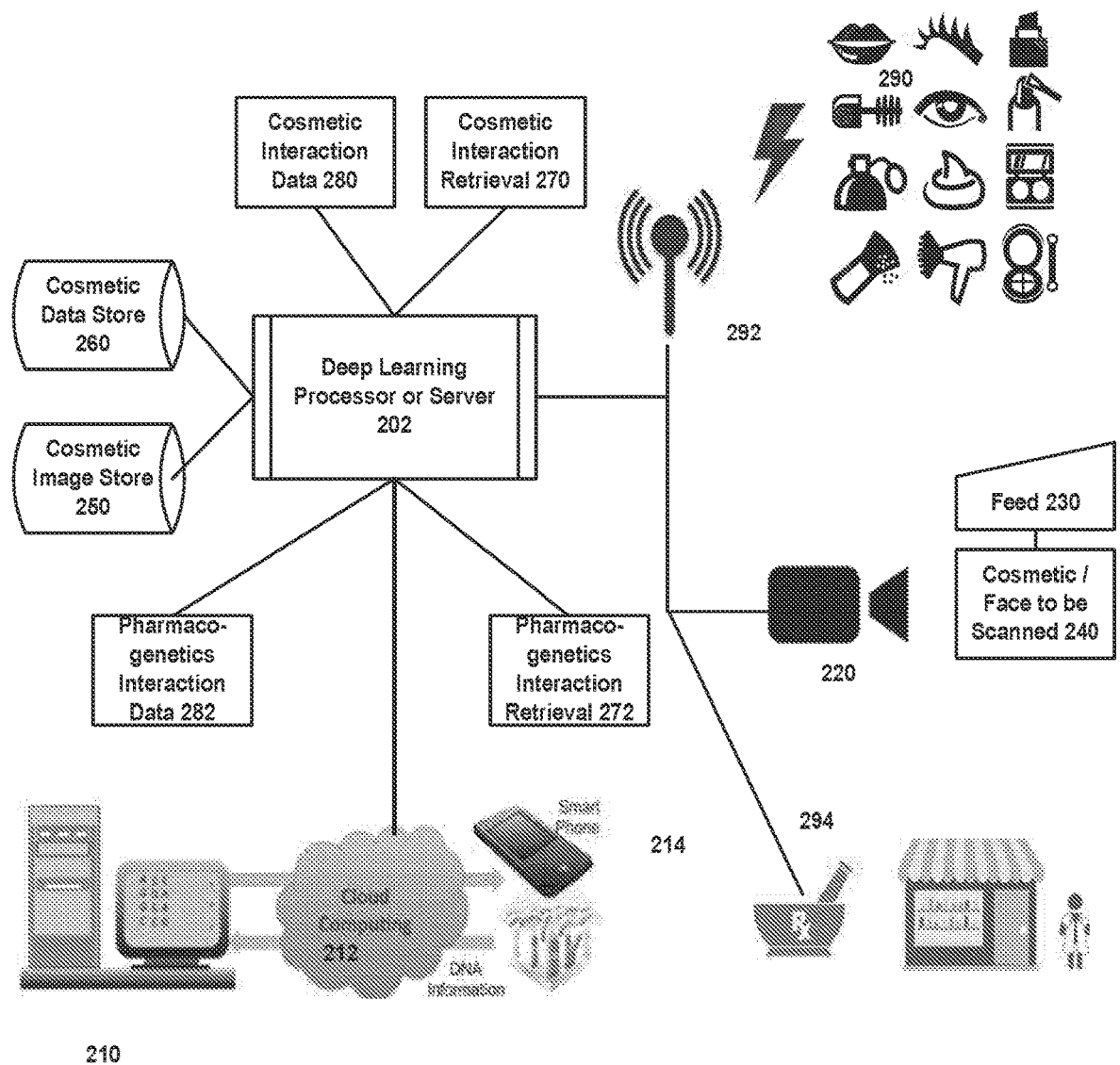
FIG. 2 is a schematic illustration of a data processing system configured for computer management genetic information, precision medication and cosmetic material interaction information retrieval.

The process shown in FIG. 1B can be implemented within a data processing system. In further illustration, FIG. 2 schematically depicts a data processing system configured for computer visualization of cosmetic materials for cosmetic material interaction information retrieval. The system can include a host computing platform 202 coupled to a camera 220 such as a digital still camera or digital video camera. The camera 220 can be focused on a marshalling point 240 provided by a marshalling apparatus 230, for example gravity feed or isolation chamber or miniature conveyor belt. The host computing platform 202 also can be communicatively coupled a cosmetic material image data store 250 of known substances and corresponding known identifying content visually disposed on the known substances. The host computing platform 202 additionally can be communicatively coupled to a cosmetic material interaction data store 260 providing cosmetic material interaction data for different substances relative to other substances including prescription and over-the-counter cosmetic materials, vitamins and herbal remedies, and food products.

In one embodiment of FIG. 2, multiple different substances such as cosmetic materials, over-the-counter health materials or even vitamins and herbal remedies can be provided to a marshalling apparatus such as a gravity feed or miniature conveyor belt or even a chamber. The marshalling apparatus can isolate an individual one of the different substances for imaging by camera 220, for example a charge coupled device (CCD) driven digital camera or video recorder. The camera 220 can capture an image of each individual one of the different substances 110A, 110B, 110N and computer visualization for cosmetic material interaction information retrieval logic 300 can process each captured image to detect identifying content disposed on each of the different substances such as a pill marking or code. The computer visualization for cosmetic material interaction information retrieval logic 300 in turn can compare the identified content to a data store of known substances 140 to identify each of the different substances. The computer can lookup not only known cosmetic material interactions for each of the different substances, but also known cosmetic material interactions between the identified ones of the substances and pharmacogenetics impact on the individual patient. Thereafter, a cosmetic material interaction report can be produced indicating the known cosmetic material interactions between the identified ones of the substances.

The host computing platform 202 can support the execution of computer scanning or visualization for cosmetic material interaction information retrieval logic 270. The logic can include program code enabled to acquire imagery of different substances in the marshalling point 240. The program code further can be enabled to locate and retrieve identifying content disposed on the different substances and to look up the identifying content in the cosmetic material image data store 250 in order to identify each of the substances. The program code yet further can be enabled to retrieve from cosmetic material interaction data store 260 cosmetic material interactions for each of the identified substances and to particularly correlate the retrieved cosmetic material interactions to different ones of the substances so that relative cosmetic material interactions can be determined for the substances. Finally, the program code can be enabled to render a report of cosmetic material interaction data in a graphical user interface display 280 of cosmetic material interaction data.

The computing platform 202 also receives pharmacogenetics interaction 282. Notably, the host computing platform 202 can support the execution of computer visualization for pharmacogenetics interaction information retrieval logic 272. Genetic information is captured by high speed gene sequencing machine 210 that uploads gene data to a cloud computing network 212. The doctors, pharmacists, or consumers can access DNA information using mobile computers such as smart phone 214, for example.

The system can have wireless communication 292 with the medication's labels. For example, the labels can have RF tags or NFC tags that provide upon inquiry FDA required labeling contents. In one embodiment, the content can be genomic biomarkers; cosmetic material exposure and clinical response variability; risk for adverse events; genotype-specific dosing; polymorphic cosmetic material target and disposition genes; and treatment based on the biomarker. NFC tags are passive devices and operate without a power supply of their own and are reliant on an active device to come into range before they are activated. To power these NFC tags, electromagnetic induction is used to create a current in the passive device. Active devices, such as a reader or a smartphone, are responsible for generating the magnetic field with a simple coil of wire, which produces magnetic fields perpendicular to the flow of the alternating current in the wire. To reduce power, NFC operates over just a few inches, rather than the meters in other types of wireless communication.

The system can be used to provide personalized medicine through custom chemical compounding 294 or custom production of a cosmetic material whose various properties (e.g. dose level, ingredient selection, route of administration, etc.) are selected and crafted for an individual patient (in contrast to mass-produced unit doses or fixed-dose combinations).

The genetic scan in 70 can be generated by gene sequencing machines. DNA sequencing is the process of determining the precise order of nucleotides within a DNA molecule. It includes any method or technology that is used to determine the order of the four bases-adenine, guanine, cytosine, and thymine—in a strand of DNA. Various high speed sequencers can be used. For example, Nanopore DNA sequencing is based on the readout of electrical signals occurring at nucleotides passing by alpha-hemolysin pores covalently bound with cyclodextrin. The DNA passing through the nanopore changes its ion current. Oxford Nanopore Technologies offers a handheld sequencer capable of generating more than 150 megabases of sequencing data in one run. More information is disclosed in U.S. Pat. No. 9,127,313, the content of which is incorporated by reference.

Another approach uses measurements of the electrical tunnelling currents across single-strand DNA as it moves through a channel. Depending on its electronic structure, each base affects the tunnelling current differently, allowing differentiation between different bases. The use of tunnelling currents has the potential to sequence orders of magnitude faster than ionic current methods and the sequencing of several DNA oligomers and micro-RNA has already been achieved. Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identify its sequence in the DNA being sequenced. Mass spectrometry may be used to determine DNA sequences. Matrix-assisted laser desorption ionization time-of-flight mass spectrometry, or MALDI-TOF MS, has specifically been investigated as an alternative method to gel electrophoresis for visualizing DNA fragments. With this method. DNA fragments generated by chain-termination sequencing reactions are compared by mass rather than by size. The mass of each nucleotide is different from the others and this difference is detectable by mass spectrometry. Single-nucleotide mutations in a fragment can be more easily detected with MS than by gel electrophoresis alone. MALDI-TOF MS can more easily detect differences between RNA fragments, so researchers may indirectly sequence DNA with MS-based methods by converting it to RNA first. In microfluidic Sanger sequencing the entire thermocycling amplification of DNA fragments as well as their separation by electrophoresis is done on a single glass wafer (approximately 10 cm in diameter) thus reducing the reagent usage as well as cost. Microscopy-based technique directly visualizes the sequence of DNA molecules using electron microscopy. RNAP sequencing is based on use of RNA polymerase (RNAP), which is attached to a polystyrene bead. One end of DNA to be sequenced is attached to another bead, with both beads being placed in optical traps. RNAP motion during transcription brings the beads in closer and their relative distance changes, which can then be recorded at a single nucleotide resolution. The sequence is deduced based on the four readouts with lowered concentrations of each of the four nucleotide types, similarly to the Sanger method. Other high speed gene sequencers can be used.

In another embodiment, a spectrophotometer for nucleic acid measurement can be used to determine the average concentrations of the nucleic acids DNA or RNA present in a mixture, as well as their purity. To date, there are two main approaches used by scientists to quantitate DNA or RNA. These are spectrophotometry and fluorescence tagging. Spectrophotometric analysis is based on the principles that nucleic acids absorb ultraviolet light in a specific pattern. In the case of DNA and RNA, a sample that is exposed to ultraviolet light at a wavelength of 260 nanometres (nm) will absorb that ultraviolet light. The resulting effect is that less light will strike the photodetector and this will produce a higher optical density (OD). Raman spectroscopy involces scattering light photons. Essentially, most photons scatter following a pattern known as 'Rayleigh scattering', but about 1 in a million particles scatter non-elastically, in the 'Raman scattering' pattern. Raman spectroscopy is capable of identifying the radiation of those photons as it is absorbed and re-emitted by materials. And every material it comes into contact with comes with its own unique 'signature'. These effects are created with a specific laser, and the precise pattern that is generated by these photons practically reveal the signature of whatever it comes into contact with, allowing scientists to identify even very minute particles.

An open source spectrophotometer called ramanPi—Raman Spectrometer can be used, the content of which is incorporated by reference. The spectrometer portion uses the Crossed Czerny-Turner Configuration and at each point in the optical system:

1. The laser emits a 532 nm (green) beam of light.
2. The 532 nm Pass Filter only allows the 532 nm (green) light to pass, and filters out anything else.
3. The Cube Beam Splitter passes half of the light on to the Objective Lens, and the other half into the Beam Dump.
4. The Objective Lens focuses the light down to a tiny point in the sample.
5. The light in the sample interacts with the molecules, and depending on vibrations, bond angles, etc. the light is shifted from 532 nm (green) to other colors/frequencies.
6. Some of the shifted light and a lot of the original laser light is reflected back into the Objective Lens and is collimated back to the Cube Beam Splitter.
7. The Cube Beam Splitter reflects half of the light to the Filter Assembly and half back into the laser.
8. The Filter Assembly contains two Edge Filters which block the 532 nm (green) laser light and allow the other colors to pass. Since this is a low cost system, two edge filters are used instead of one Notch Filter . . . and so two separate exposures are taken and the images are stacked.
9. The Vertical Aperture (slit) controls the amount of light that enters the spectrometer section, and is a determining factor in spectral resolution.
10. The light from the slit is reflected off the Collimating Mirror on its way to the Diffraction Grating.

11. The Diffraction Grating acts like a Prism and divides the light into separate colors. Since the light originated as 532 nm (green), and the shift is typically fairly minor, this light may be close to the original color . . . but also may be red (lower frequency) or even blue (higher frequency).

12. The light reflected from the Diffraction Grating is reflected by the Imaging or Focusing Mirror onto the Detector Array.

13. The spectra derived from the above process is reflected by the Imaging Mirror onto the CCD Array where it is captured by the raspberryPi for processing. One image is taken with the first Edge Filter, then another exposure with the next Edge Filter and then some software to stack the images is used together along with some signal processing and possibly multiple exposures to gain as much brightness as possible so the computer can correctly analyze the spectra.

Gas chromatography-mass spectrometry (GC-MS) can be used to analyze metabolites from biological samples. Compared with the typical GC-MS system, comprehensive two dimensional gas chromatography-time-of-flight mass spectrometry (GC×GC-TOF MS) is a more powerful analytical platform, with an order-of-magnitude increase in separation capacity, an increase in signal-to-noise ratio and dynamic range, and improvement of mass spectral deconvolution and similarity matches. The GC×GC-TOF MS instrument employs two capillary GC columns of different polarities connected via a thermal modulator to achieve a high degree of separation of metabolites. Typically, the second column is short (0.5-2 m) and operated at a higher temperature than the first column (10-60 m). The metabolites coeluted from the first GC column are further separated in the second column because of the difference in column temperature and stationary phase. The further separated metabolites are directed to a time-of-flight mass spectrometry system for detection.

One embodiment of the system applies pharmacogenomic information to select the best medication and identify people who need an unusually high or low dose. This is in addition to clinical factors, such as a patient's age, weight, sex, and liver and kidney function. Pharmacogenomics (sometimes called pharmacogenetics) is focused on understanding how genes affect individual responses to medications and to help doctors select the cosmetic materials and dosages best suited for each person. Pharmacogenomics looks at variations in genes for proteins that influence cosmetic material responses. Such proteins include a number of liver enzymes that convert medications into their active or inactive forms. Even small differences in the genetic sequences of these enzymes can have a big impact on a cosmetic material's safety or effectiveness. One example involves a liver enzyme known as CYP2D6. This enzyme acts on a quarter of all prescription cosmetic materials, including the painkiller codeine, which it converts into the cosmetic material's active form, morphine. The CYP2D6 gene exists in more than 160 different versions, many of which vary by only a single difference in their DNA sequence, although some have larger changes. The majority of these variants don't affect cosmetic material responses. Some people have hundreds or even thousands of copies of the CYP2D6 gene (typically, people have two copies of each gene). Those with extra copies of this gene manufacture an overabundance of CYP2D6 enzyme molecules and metabolize the cosmetic material very rapidly. As a result, codeine may be converted to morphine so quickly and completely that a standard dose of the cosmetic material can be an overdose. On the other end of the spectrum, some variants of CYP2D6 result in a nonfunctional enzyme. People with these variants metabolize codeine slowly, if at all, so they might not experience much pain relief. For these people, doctors might prescribe a different type of pain reliever. Pharmacogenomic information can cover dosage guidance, possible side effects or differences in effectiveness for people with certain genomic variations—can help doctors tailor their cosmetic material prescriptions for individual patients. The system applies pharmacogenomic data to develop and market cosmetic materials for people with specific genetic profiles. The system can identify the genetic basis for certain serious side effects, cosmetic materials could be prescribed only to people who are not at risk for them. As a result, potentially lifesaving medications, which otherwise might be taken off the market because they pose a risk for some people, could still be available to those who could benefit from them. For example, a few cosmetic material and gene associations are listed in the Appendix.

It will be recognized by the skilled artisan that while the computer visualization for cosmetic material interaction information retrieval logic 270 is shown to execute in a single host computing platform 202, the invention is not so limited and the computer visualization for cosmetic material interaction information retrieval logic 270 also can be distributed in form across multiple different computing platforms. Further, the camera 220 and marshalling apparatus 230 can be located remotely from the host computing platform 202 whilst providing acquired imagery to the host computing platform 210 over a computer communications network, whether wireless or wirebound. Yet further, either or both of the cosmetic material image data store 250 and the cosmetic material interaction data store 260 can be remotely disposed from the host computing platform 202 and accessible over a computer communications network, whether wireless or wirebound.

In general, database 260 includes information about cosmetic products, which may include their price, their availability, their attributes (e.g., color, coverage, viscosity, luminosity, sheen, sparkle, etc.), manufacturers, etc. Database 260 may also include information about public figures, such as celebrities. Such public figure information can include data about the public figure's skin tone, bone structure, face shape, and cosmetic products that are used by the public figure. Database 260 may also include demo, review, and/or instructional information, such as references to online videos, articles, pamphlets, etc., that can be disseminated to a user based on a recommend cosmetic product, and/or based on a matched public figure. Database 260 may also include advertising information, which can be disseminated to users through system in any appropriate context or manner.

As noted, database 260 can include information about public figures, such as celebrities, such as cosmetic products and styles that are used by public figures. As such, computer architecture 100 can be used to help a person to identify public figures that have skin and facial features that are similar to their own skin and facial features, and to leverage knowledge of what cosmetic products the public figure uses—and how the public figure uses those products—for cosmetic recommendations. Additionally or alternatively, computer architecture 100 can even be used to help a person not having skin tones and facial features similar to a desired public figure to duplicate that public figure's look on their own skin tones and facial features. As such, computer may adjust color recommendations to duplicate a public figure's look on the user's skin tone and features.

In some embodiments, the system may be configured to simulate application of one or more cosmetic products to the user's face. For example, the system may visually present a generic image of a face, or even a photographic capture of the user's face, and simulate what the generic image or the photograph of the user's face would look like with one or more cosmetic products applied thereto. The system may provide functionality for adjusting the virtual application of each cosmetic product (e.g., order, quantity, location, etc.), for selecting substituting different products, for selecting different combinations of products, etc.

In some embodiments, the system may be configured to instruct a user how to apply cosmetic products. For example, an example instruction image visually shows a user where and/or how to apply different cosmetic products. Such instruction image may guide a user through techniques for emphasizing certain facial features, for deemphasizing certain facial features, for achieving desired color or texture features, etc. Such instruction image may include the user's own face, or may be selected from one or more generic models. When the system provides cosmetic recommendations, the devices can provide rich interactive functionality to the user for filtering and comparing cosmetic products. For example, the user may be enabled to filter products by price, manufacturer, public figure, attribute (e.g., color, coverage, etc.), availability, environmental friendliness, animal friendliness, toxicity, etc. In another example, a user may be enabled two visually compare two or more products side-by-side, such as to compare color, texture, etc. For example, when a user is looking for a substitute of a remnant, the testing device 104 may display the image that was captured of the remnant (or a derivation thereof) side-by-side with images of candidate replacement products.

As indicated previously, database 260 may also include demo, review, and/or instructional information that can be disseminated to a user based on a recommend cosmetic product, and/or based on a matched public figure. Such information may be disseminated to a user by way of electronic mail. SMS/MMS messaging, physical printouts, wireless transfer, communication with a corresponding mobile application, etc. In addition, the system may be configured to enable a user to purchase recommended cosmetic products at the system, such as for home shipment or in-store pickup.

The disclosed methods include measuring skin health-associated SNPs or other genetic markers in the biological sample obtained from the subject and comparing that to a control or reference value. In some examples, a subject's genetic potential is determined in five areas of skin health by analyzing one or more skin health-associated SNPs or other genetic markers associated with the five areas of skin health in a sample obtained from the subject. The one or more areas of skin health can include assessing the following factors: collagen formation, sun protection, antioxidant protection, glycation protection and inflammation control. Methods of isolating nucleic acid molecules from a biological sample are routine and known to those of ordinary skill in the art, for example using PCR to amplify the molecules from the sample, or by using a commercially available kit to isolate DNA. Nucleic acid molecules isolated from buccal swab samples or any other biological sample can be amplified using routine methods to form nucleic acid amplification products. Exemplary methods of isolating DNA and detecting SNPs associated with one or more skin conditions or disorders are described below in the Molecular Methods Section.

a. Hyaluronic Acid Rating

Numerous roles of HA in the body have been identified. It plays an important role in the biological organism, as a mechanical support for the cells of many tissues, such as the skin, tendons, muscles and cartilage. HA is involved in key biological processes, such as the moistening of tissues, and lubrication. It is also suspected of having a role in numerous physiological functions, such as adhesion, development, cell motility, cancer, angiogenesis, and wound healing. Due to the unique physical and biological properties of HA (including viscoelasticity, biocompatibility, biodegradability), HA is employed in a wide range of current and developing applications within ophthalmology, rheumatology, drug delivery, wound healing and tissue engineering.

b. Collagen Rating

Collagen is a principal structural protein of the skin and plays a role in skin firmness, fullness or plumpness and well as wrinkles. The speed of collagen synthesis and breakdown is influenced by a subject's genetic makeup. Genes known to be involved in slowing the breakdown and/or degradation of collagen fibers in skin can be collagen formation factors. A higher score in the disclosed assay of collagen formation factors indicates a more ideal genetic disposition for slowing the breakdown of collagen. A lower score indicates a greater likelihood of collagen breakdown, an MMP-1 and collagen imbalance, a decrease in tissue remodeling, ineffective wound healing and thus, the need for a skincare and/or nutritional treatment to prevent, inhibit or reduce one or more of these factors. A need for treating a collagen formation associated condition can also be identified by the presence of one or more of the following: prolonged skin redness; poor wound healing; accelerated aging; and/or skin laxity and/or sagging.

c. Sun Protection Rating

Ultraviolet (UV) exposure causes skin deterioration, premature skin aging, and a host of other profound changes to your skin. Exposure to UV light from the sun accounts for 90% of the symptoms of early skin aging. A subject's genetic makeup influences the effect that UV exposure on skin. A higher score with the present assay indicates a greater natural genetic protection. A lower score indicates likelihood of increased UV free radical damage, irregular cellular function, increased mitochondrial damage, DNA structural damage and ineffective melanogenesis and thus, the need for a skincare and/or nutritional treatment to prevent, inhibit or reduce one or more of these factors. A need for treating a sun protection associated condition can also be identified by the presence of one or more of the following: blemishes and redness; excess pigmentation, freckles and/or brown spots: skin thinning; fine lines; rough surface texture; enlarged pores; and/or redness/broken capillaries.

d. Antioxidant Protection Rating

The oxidation phenomenon caused by free radicals is recognized as one of the leading causes of skin aging. A primary factor in determining damage from free radicals is controlled by genes known to be associated with antioxidant activities. A higher score indicates an increased genetic advantage for antioxidant protection. A lower score indicates likelihood of heightened free-radical cellular destruction, premature cell death; increased mitochondrial damage; decreased antioxidant functioning, decreased quinone detoxification and thus, the need for a skincare and/or nutritional treatment to prevent, inhibit or reduce one or more of these factors. A need for treating an antioxidant protection associated condition can also be identified by the presence of one or more of the following: uneven skin tone, irregular pigmentation; rough skin texture; acne and rosacea; excess skin dryness or oiliness; and/or accelerated aging and/or thinning of skin.

e. Glycation Protection Rating

Advanced Glycation End Products (AGEs) are the end result of a glucose-driven process known as glycation. Glycation is implicated in accelerated skin aging, leading to wrinkling, dryness, sagging, and laxity in your skin. A subject's score indicates the subject's genetic protection against glycation: a higher score indicates a more optimal predisposition. A lower score indicates likelihood of glucose/collagen cross-linking: decreased skin elasticity; stiffened collagen fibers, weak dermal epidermal junctions; increased production of free radicals, and thus, the need for a skincare and/or nutritional treatment to prevent, inhibit or reduce one or more of these factors. A need for treating a glycation protection associated condition can also be identified by the presence of one or more of the following: heavy wrinkles and/or skin folds; accelerated aging; sagging skin; cracking and thinning skin; and/or uneven skin texture.

f. Inflammation Rating

Inflammation is skin's first line of defense against foreign substances like bacteria and chemicals. However, excessive inflammation is one of the most common causes of early onset skin deterioration and aging. A subject's genetic makeup play a role in the regulation of inflammation: a higher score indicates a greater capacity to reduce inflammation.

A lower score indicates possible irregular tissue healing, decreased cellular defense, overactive inflammatory signaling, enhanced sensitivity, decreased efficacy of the detoxification process, increased production of free radicals and thus, the need for a skincare and/or nutritional treatment to prevent, inhibit or reduce one or more of these factors. A need for treating an inflammation control factor associated condition can also be identified by the presence of one or more of the following: skin redness; acne rosacea; rashes, swelling and/or dermatitis (eczema); accelerated aging; and/or enhanced sensitivity to foreign substances like bacteria and chemicals.

iii. Providing a Skin Profile to a Subject

Following the measurement of one or more SNPs associated with skin health, the results, findings, diagnoses, predictions and/or treatment recommendations can be provided to the subject. For example, the results, findings, diagnoses, predictions and/or treatment recommendations can be recorded and communicated to technicians, physicians and/or patients or clients. In certain embodiments, computers can be used to communicate such information to interested parties, such as, clients, patients and/or the attending physicians. Based on the measurement, the therapy or protocol administered to a subject can be started, modified not started or re-started (in the case of monitoring for a reoccurrence of a particular skin condition/disorder).

In some examples, the output can provide a recommended therapeutic regimen or skin care protocol. In some examples, the test may include determination of other clinical information.

In some embodiments, the disclosed methods include one or more of the following depending on the subject's skin profile: a) prescribing or recommending a protocol or treatment regimen for the subject if the subject's determined profile is considered to be high or medium risk, sub-optimal or deficient in one or more areas of skin health; b) not prescribing or recommending a protocol or treatment regimen for the subject if the subject's determined skin profile is considered to be optimal in the evaluated skin areas; c) administering a protocol or treatment to the subject if the subject's determined diagnosis or profile is considered to be high or medium risk or sub-optimal or deficient in one or more areas of skin health or appearance: d) not administering a protocol or treatment regimen to the subject if the subject's determined skin profile is considered to be optimal in the evaluated skin areas. In an alternative embodiment, the method can include recommending one or more of a)-d).

In addition to DNA testing for skin tone, the present inventor also contemplates camera based skin tone detection. In this embodiment, the system comprises an act of capturing a face scan. Act can include capturing a photographic image, spectrophotometer scan, etc. of a user's face using one or more of the sensing devices 105a. In capturing the face scan, the system may provide for predefined and controlled lighting conditions, and/or may adjust the white balance or other color parameters of a captured photographic image. The system also comprises an act of determining a skin tone. The system can include determining, from the face scan, a skin tone of the user's face. For example, the system may use software algorithms and analysis module to ascertain the skin tone, or the testing device may upload the face scan to the servers for processing.

The method includes identifying cosmetic products) based on the skin tone. For example, the system includes identifying, based on the skin tone of the user's face, one or more cosmetic products that are recommended for the user. For example, the system may identify cosmetic products in database 260 that are recommended for the user based on the skin tone. Such recommendation may be made based on identifying one or more cosmetic products having a color that matches the user's skin tone, or having a color that compliments the user's skin tone. The identification of products may be based on price, brand/manufacturer, product line, public figure, etc.

The system provides a cosmetic recommendation including the identified cosmetic product(s). The system can include providing a cosmetic recommendation to the user, the cosmetic recommendation including the one or more cosmetic products that are recommended for the user based on the skin tone of the user's face. For example, the system may formulate a cosmetic recommendation. The system can send then communicate the cosmetic recommendation to the user. Testing device 104 can communicate the cosmetic recommendation using the output module 106 and output devices 106a visually, with a printout, or electronically to one or more of a smartphone, a tablet computer, a desktop computer, or a laptop computer.

Any skin surface can be treated using the methods provided herein. By "skin surface" is intended the stratum corneum, epidermis, dermis or any other layer of the skin thereof. Skin surfaces that can be treated include, but are not limited to face, scalp, neck, chest, back, torso, arms, legs, hands or feet including periorbits, lips, cheeks, nasolabial folds, forehead, chin, neck, upper lip rhytides, or any combination thereof. The skin of any facial surface can be treated using the methods provided herein. The method can be applied to any facial or scalp area and/or to any body surface area, with other immediate areas of application being the chest, neck and body. More than one skin surface can be treated during the same treatment period.

Improving skin quality includes reversing, slowing the progression of, supporting the healthy function of or preventing skin changes associated with natural or innate aging or other biological or disease effects. As used herein, "prevent" and variations thereof refer to any degree of delaying the onset of skin changes. For example, improving skin quality includes the reversal, slowing the progression of, or prevention of skin changes associated with sun damage or photo aging, skin changes associated with exposure to sunlight or other forms of actinic radiation (for example, UV radiation and tanning booths). As another example, improving skin quality also can include reversing, slowing the progression of, or preventing skin changes resulting from extrinsic factors, including, but not limited to, radiation, air pollution, sun, UV rays, wind, cold, dampness, heat, chemicals, smoke, cigarette smoking, and combinations thereof. Improving skin quality also can include reversing, preventing or reducing scarring the can result, for example, from certain skin conditions (for example, acne), infections (for example, leishmaniasis), or injury (for example, abrasions, punctures, lacerations, or surgical wounds). Improvements to the skin can also include at least one of the following: reducing red, brown or any other abnormal pigment making facial lines appear less noticeable, making facial lines and/or wrinkles feel plumped, improving the appearance of suborbital lines and/or periorbital lines, improving the appearance of crow's feet, reducing and/or diminishing the appearance of wrinkles, particularly facial wrinkles on the cheeks, forehead (for example, perpendicular wrinkles between eyes, horizontal wrinkles above the eyes), and/or around the mouth, and particularly deep wrinkles, folds, or creases, improving skin suppleness smoothness texture and tone, reducing and/or eliminating fine and/or deep lines, folds and creases, and smoothing skin. Skin changes treatable by practicing the methods and using the assays disclosed herein include, for example, wrinkles (including, but not limited to, human facial wrinkles), creases, furrows, folds and fine lines, deepening of skin lines, thinning of skin, reduced scarring, yellowing, browning or reddening of the skin, mottling, hyperpigmentation, appearance of pigmented and/or non-pigmented age spots, leatheriness, loss of elasticity, loss of recoilability, loss of collagen fibers, abnormal changes in the elastic fibers, deterioration of small blood vessels of the dermis, formation of solar increased visible vasculature on the skin surface, inflammation including redness, dryness or irritation of the skin or any other skin abnormality or combinations thereof.

Improving skin quality includes decreasing, reducing, and/or minimizing one or more of the skin changes discussed above. Improving skin quality can result in the skin having a more youthful and healthy appearance. Improving skin quality can result in the skin having a smoother, hydrated (less dry), or less scaly appearance. For example, in certain embodiments, improving skin quality can include a reduction in roughness, dryness, irritation or scaliness. Improving skin quality includes the effacement and improvement of lines and wrinkles, improvement in turgor, and tonicity, with the observed desired effects of lifting and tightening.

The textural qualities of the skin can be improved, including softness, suppleness, and smoothness, leading to enhancement of luster, clarity and brightness. Additional and important qualities of the skin that can be subjectively and objectively measured include, but are not limited to skin laxity, or conversely skin tightness, and the presence and degree of textural fine lines and coarser lines within the skin.

These are the same qualities by which the external aspects of appearance (for example, aging of skin) are judged. Improvement in these qualities by the method of treatment and kits disclosed herein result in a benefit based on visual judgment of appearance. Changing a quality of the skin by the methods disclosed herein lessens the appearance of aging of the skin.

Desired benefits may include not only physiologic benefit to the skin, but therapeutic and pharmacologic benefits, such as possible malignancy prevention and treatment. Benefits may also include acne treatment and suppression, by including compositions which suppress sebaceous glandular activity, enhance bacterial suppression, or enhance retinoid delivery into the skin.

Exemplary Compositions that can be customized to skin treatment includes:

i. Antioxidant Cleanser

In some examples, an antioxidant cleanser is applied topically to a skin surface as needed, such as to prevent, reduce, or inhibit one or more signs or symptoms associated with high or medium risk or sub-normal or deficient skin health factors. In one example, the antioxidant cleanser comprises: sodium lauryl glucose carboxylate; lauryl glucoside; coco-glucoside; cocamidopropyl betaine; glyceryl oleate; glycerin; caprylyl glycol; *citrus grandis* (grapefruit) peel oil; panthenol; *Solanum lycopersicum* (tomato) extract; *citrus Aurantium bergamia* (bergamot) fruit oil; *Thymus vulgaris* (thyme) extract; algae extract, aloe barbadensis leaf; and *citrus medica limonum* (lemon) peel oil.

ii. Balancing Toner

In some examples, a balancing toner is applied topically to a skin surface as needed, such as to prevent, reduce, or inhibit one or more signs or symptoms associated with high or medium risk or sub-normal or deficient skin health factors. In one example, the balancing toner comprises: methyl gluceth-20; glycerin; caprylyl glycol; sodium PGA; panthenol; *citrus grandis* (grapefruit) peel oil; *Thymus vulgaris* (thyme extract); *citrus aurantium amara* (bitter orange) extract; *hamamelis virginiana* (witch hazel) bark/leaf/twig extract; *glycine soja* (soybean) seed extract; *Solanum lycopersicum* (tomato) extract; *citrus aurantium bergamia* (bergamot) fruit oil; aloe barbadensis leaf; ascorbic acid; tocopheryl acetate; retinyl palmitate; and bioflavonoids.

iii. Wrinkle Treatment Serum

In some examples, a wrinkle treatment serum is applied topically to a skin surface as needed, such as to prevent, reduce, or inhibit one or more signs or symptoms associated with high or medium risk or sub-normal or deficient skin health factors. In one example, the wrinkle treatment serum comprises: acetyl octapeptide-3 (SNAP-8); capryly glycol; glycerin; palmitoyl oligopeptide, palmitoyl tetrapeptide-7 (also known as Matrixyl-300); hyaluronic acid; *Solanum lycopersicum* (tomato) extract; *Thymus vulgaris* (thyme) extract; aloe barbadensis leaf; *leontopodium alpinum* (edelweiss) flower/leaf extract; *glycine soja* (soybean) seed extract; *citrus grandis* (grapefruit) peel oil; and allantoin.

iv. Vitamin C Treatment Serum

In some examples, a vitamin C treatment serum is applied topically to a skin surface as needed, such as to prevent, reduce, or inhibit one or more signs or symptoms associated with high or medium risk or sub-normal or deficient skin health factors. In one example, the vitamin C treatment serum comprises: cyclopentasiloxane, dimethicone crosspolymer, cyclomethicone; sodium ascorbyl phosphate; idebenone; caprylyl glycol; *citrus grandis* (grapefruit) peel oil; magnesium ascorbyl phosphate; *citrus aurantium dulcis* (orange) peel oil; aloe barbadensis leaf; retinyl palmitate; and tocopherol.

v. Calming Treatment Serum

In some examples, calming treatment serum is applied topically to a skin surface as needed, such as to prevent, reduce, or inhibit one or more signs or symptoms associated with high or medium risk or sub-normal or deficient skin health factors. In one example, the calming treatment serum comprises: glycerin; sodium cocoyl amino acids, sarcosine, potassium aspartate, magnesium aspartate, caprylyl glycol;

hyaluronic acid; caprylic/capric triglyceride; *citrus grandis* (grapefruit) peel oil; *glycine soja* (soybean) seed extract; *Thymus vulgaris* (thyme) extract; *arnica montana* flower extract; *Solanum lycopersicum* (tomato) extract; *leontopodium alpinum* (edelweiss) flower/leaf extract; ale barbadensis leaf; and *epilobium angustifolium* (canadian willow) extract.

vi. Hyaluronic Moisture Treatment Serum

In some examples, hyaluronic moisture treatment serum is applied topically to a skin surface as needed, such as to prevent, reduce, or inhibit one or more signs or symptoms associated with high or medium risk or sub-normal or deficient skin health factors. In one example, the hyaluronic moisture treatment serum comprises: hyaluronic acid; sodium PGA; caprylyl glycol; glycerin; panthenol; *avena sative* (oat) kernel extract; *Thymus vulgaris* (thyme) extract; *saccharomyces*/silicon ferment, *saccharomyces*/copper ferment, *saccharomyces*/iron ferment, *saccharomyces*/zinc ferment; aloe barbadensis leaf; *leontopodium alpinum* flower/leaf extract; and allantoin.

vii. Antioxidant Moisturizer

In some examples, an antioxidant moisture is applied topically to a skin surface as needed, such as to prevent, reduce, or inhibit one or more signs or symptoms associated with high or medium risk or sub-normal or deficient skin health factors. In one example, the antioxidant moisture comprises: polyacrylamide; glycerin; sorbitol, caprylic/capric triglyceride, squalene, cyclomethicone, caprylyl glycol, hyaluronic acid, glycoproteins, *citrus grandis, Thymus vulgaris* (thyme) extract, thioctic acid, *Solanum lycopersicum* (Tomato) extract, *camellia* oleifera (green tea) leaf extract, *Oryza sativa* (rice) bran oil, tocopheryl acetate, aloe barbadensis leaf, ubiquinone, and *glycine soja* (soybean) seed extract viii. Collagen Composition In some examples, a subject determined to have sub-normal or deficient levels of collagen protection factors, is administered a collagen defense composition to reduce, inhibit, and/or prevent one or more signs associated with high or medium risk or sub-normal or deficient levels of collagen protection factors. In some examples, the collagen defense composition is in tablet/capsule form and is administered to the subject twice daily and includes the following: Choline (as Choline-Stabilized Orthosilicic Acid), and Silicon (as Choline-Stabilized Orthosilicic Acid).

ix. Sun Composition

In some examples, a subject determined to have sub-normal or deficient levels of sun protection factors, is administered a sun defense composition to reduce, inhibit, and/or prevent one or more signs associated with high or medium risk or sub-normal or deficient levels of sun protection factors. In some examples, a sun defense compositions includes trans-resveratrol and quercetin. In some examples, the sun defense composition is in tablet/capsule form and is administered to the subject twice daily and includes the following: Trans-Resveratrol (*Polygonum Cuspidatum*), Quercetin Dihydrate, Lecithin, Microcrystalline Cellulose, Dicalcum Phosphate, Silicon Dioxide, Vegetable Stearate x. Antioxidant Composition In some examples, a subject determined to have sub-normal or deficient levels of antioxidant protection factors, is administered an antioxidant defense composition to reduce, inhibit, and/or prevent one or more signs associated with high or medium risk or sub-normal or deficient levels of antioxidant protection factors. In some examples, the antioxidant defense composition is in tablet/capsule form and is administered to the subject three times daily and includes the following: Vitamin A (as Natural Mixed Carotenoids Complex), Alpha Carotene 2.5, Beta Carotene, Acerola (*Malpighia Glabra*), High Gamma Mixed Tocopherols, Grape Seed Extract (Wis *Vinifera*), Curcumin C3 Complex® (Curcumin, Bisdemethoxy Curcumin, Demethoxy Curcumin), Garlic (*Allium Sativum*), Tocotrienols (from Annatto Bean), *Ginkgo Biloba*, Quercetin, Rutin, Clove (*Syzygium Aromaticum*), Allspice (*Pimenta Dioca*), Sweet Basil (*Ocimum Basilicum*), Sage (*Salvia Officinalis*), Rosemary (Rosemarinus Officinalus), *Polygonum Cuspidatum* (50% Trans-Resveratrol), Lutein (*Tagetes Erecta* L) (Marigold Lutein Esters), Lycopene, Microcrystalline Cellulose, Silicon Dioxide, Stearates (Vegetable Source).

xi. Glycation Composition

In some examples, a subject determined to have sub-normal or deficient levels of glycation protection factors, is administered a glycation defense composition to reduce, inhibit, and/or prevent one or more signs associated with high or medium risk or sub-normal or deficient levels of glycation protection factors. Excess sugar in the body is a primary cause of premature skin aging because of its role in a process called glycation. Glycation occurs when blood sugar binds to collagen and elastin fibers, essentially "car-melizing" or hardening skin. Glycated skin results in skin laxity, cracking, thinning, redness and inability to self-repair. In some examples, a glycation defense composition is administered to the subject wherein the composition comprises herbs, polyphenols and antioxidants to sugar levels and protect against glycation. In some examples, the glycation defense composition is in tablet/capsule form and is administered to the subject twice daily and includes Salacia (Salacia *Oblonga*), Fennugreek (*Trigonella Foenum-Graecum*), American *Ginseng* (*Panax Quinquefolius*), *Gymnema* (*Gymnema Sylvestre*), Banaba (Langerstroemia Spp.), Kudzu (Pueraraia *lobata*), Cinnamon (*Cinnamomum* Spp.), Microcrystalline Cellulose, and Vegetable Stearate.

xii. Inflammation Composition

In some examples, a subject determined to have high or medium risk or sub-normal or deficient levels of inflammation protection factors, is administered an inflammation defense composition to reduce, inhibit, and/or prevent one or more signs associated with skin inflammation such as skin sensitivity, redness, irritation, acne, rosacea and eczema. In some examples, an inflammation defense composition comprises n*zimes® Proprietary Blend (Protease 6.0, Protease 4.5, Trypsin 1:150). Serrazimes®, Chymotrypsin, Turmeric (*Curcuma Longa*), Boswellia (*Boswellia Serrata*), Ginger (*Zingiber* Offinale), Ouercetin, Rutin, Rosemary Extract (Rosemarinus *Officinalis*), Microcrystalline Cellulose, Silicon Dioxide, Vegetable Stearate. This inflammation defense composition is administered in tablet/capsule form, twice daily.

Providing a cosmetic recommendation may include visually simulating application of at least one cosmetic product to the scan of the user's face. Providing a cosmetic recommendation may also include providing at least one review of a cosmetic product, which may include sending the user a Uniform Resource Locator (URL) to an Internet video, review, publication, etc. In some embodiments, the cosmetic recommendation is limited by one or more filter criteria that are received from the user, such as product attributes (e.g., coverage, viscosity, luminosity, etc.), price, brand, celebrity, etc. In some embodiments, method includes identifying, from a public figure database (e.g., within database 260), at least one public figure having a skin tone that is the same as, or within a predefined color threshold to, the skin tone of the user's face. In such embodiments, the identification of cosmetic products that are recommended for the user comprises identifying, from the public figure database, one or more cosmetic products that are used by the public figure. In some embodiments, method includes receiving an identity of a public figure (e.g., from the user), and then determining, from a public figure database, a skin tone of the public figure and one or more cosmetic products that are used by the public figure. Based on this information, a color difference between the skin tone of the public figure and the skin tone of the user is determined. Then, the recommended cosmetic products include a color adjustment that allows the user to use products that are similar to the public figure's, but that work with the user's skin tone based on matching DNA characteristics or visual identification through a camera, among others. For example:

Redheads with fair to medium skin tones like Susan Sarandon, Nicole Kidman, and Julianne Moore tend to wear corals, salmon, browns, ambers, bronze, and other earth tones.

Blondes with fair skin to medium skin tones like Gwyneth Paltrow, Emma Stone, and Kirsten Dunst favor a range of pink shades.

Brunettes with fair to medium skin tones like Julia Roberts and Jennifer Garner are often seen in light rose and soft red shades.

Women with dark brown hair and fair to medium skin tones like Demi Moore, Sandra Bullock, and Penelope Cruz wear more vivid shades of rose and cherry.

Black hair and deeper skin tones such as Halle Berry and Zoe Saldana or Oprah Winfrey wear soft natural tones such as nude pinks, soft browns, and corals.

One embodiment allows selection of a color lipstick family from the DNA data. The customer can enter a specific lipstick number, or choose a color family, then choose a color from the family. The active color palette will consist of individual palettes that contain that lipstick. The customer can also enter a specific look or a selection of lipstick from a color family. If the lipstick is also in the palette recommendation based on skin tone, the color is put first in the list, and (expert fit) is added to the name.

The system can select color for the following exemplary cosmetic components:

Primer comes in formulas to suit individual skin conditions. Most are meant to reduce the appearance of pore size, prolong the wear of makeup, and allow for a smoother application of makeup. Primers are applied before foundation or eyeshadows depending on where the primer is to be applied.

Lipstick, lip gloss, lip liner, lip plumper, lip balm, lip stain, lip conditioner, lip primer, lip boosters, and lip butters: Lipsticks are intended to add color and texture to the lips and often come in a wide range of colors, as well as finishes such as matte, satin and lustre. Lip stains have a water or gel base and may contain alcohol to help the product stay on leaving a matte look. They temporarily saturate the lips with a dye. Usually designed to be waterproof, the product may come with an applicator brush, rollerball, or could be applied with a finger. Lip glosses are intended to add shine to the lips and may add a tint of color, as well as being scented or flavored for a pop of fun. Lip balms are most often used to moisturize, tint and protect the lips. They often contain SPF protection depending on what brand it is bought from.

Concealer makeup covers imperfections of the skin. Concealer is often used for any extra coverage needed to cover blemishes, undereye circles, and other imperfections. Concealer is often thicker and more solid than foundation, and provides longer lasting, more detailed coverage. Some formulations are meant only for the eye or only for the face. This product can also be used for contouring the face like ones nose, cheekbones, and jaw line to add a more defined look to the total face.

Foundation is used to smooth out the face and cover spots, acne and blemishes or uneven skin coloration. Usually a liquid, cream, or powder, as well as most recently a light and fluffy mousse. Foundation provides coverage from sheer to matt to dewey or full. Foundation primer can be applied before or after foundation to obtain a smoother finish. Some primers come in powder or liquid form to be applied before foundation as a base, while other primers come as a spray to be applied after the foundation to set the make-up and help it last longer throughout the day.

Face powder sets the foundation, giving it a matte finish, and to conceal small flaws or blemishes and can also be used to bake the foundation, so it stays on longer. Tinted face powders may be worn alone as a light foundation so that the full face does not look as caked up as it could.

Rouge, blush or blusher is cheek coloring to bring out the color in the cheeks and make the cheekbones appear more defined. Rouge comes in powder, cream, and liquid forms. Different blushes compliment different skin tones, however there is a blush for most skin tones.

Contour powder/creams are used to define the face. They can give the illusion of a slimmer face or to modify a face shape in other desired ways. Usually a few shades darker than one's own skin tone and matte in finish, contour products create the illusion of depth. A darker toned foundation/concealer can be used instead of contour products for a more natural look.

Highlight, used to draw attention to the high points of the face as well as to add glow, comes in liquid, cream, and powder forms. It often contains a substance to provide shimmer. A lighter toned foundation/concealer can be used instead of highlight to create a more natural look and warm feel.

Bronzer gives skin a bit of color by adding a golden or bronze glow and highlighting the cheekbones, as well as being used for contouring. Bronzer is considered to be more of a natural look and can be used for an everyday wear. Bronzer enhances the color of the face while adding more of a shimmery look. It comes in either matte, semi matte/satin, or shimmer finishes.

Mascara is used to darken, lengthen, thicken, or draw attention to the eyelashes. It is available in natural colors such as brown and black, but also comes in bolder colors such as blue, pink, or purple. Some mascaras include glitter flecks. There are many formulas, including waterproof versions for those prone to allergies or sudden tears. It is often used after an eyelash curler and mascara primer. Many mascaras have components to help lashes appear longer and thicker.

Eyeliner is used to enhance and elongate the size of the eye or to add a certain depth to the eye to create a certain look. For example, using white eyeliner on the waterline and inner corners of the eye helps to make the eyes look bigger and more awake.

Eyebrow pencils, creams, waxes, gels and powders are used to color, fill in and define the brows.

Nail polish is used to color the fingernails and toenails. Transparent, colorless versions may strengthen nails or as a top or base coat to protect the nail or polish.

Setting spray is used as the last step in the process of applying makeup. It keeps applied makeup intact for long periods. An alternative to setting spray is setting powder, which may be either pigmented or translucent. Both of these products claim to keep makeup from absorbing into the skin or melting off.

False eyelashes are frequently used when extravagant and exaggerated eyelashes are desired. Their basic design usually consists of human hair or synthetic materials attached to a thin cloth-like band, which is applied with an eyelash glue to the lashline. Designs vary from short, natural-looking lashes to extremely long, wispy, rainbow-colored lashes. Rhinestones, gems, and even feathers and lace occur on some false eyelash designs.

The system enables a medical model that separates patients into different groups—with beautifying decisions, practices, interventions and/or products being tailored to the individual user based on their predicted response or risk of skin disease from an ex vivo sample such as a saliva sample or buccal swab provided by the individual prior to testing.

One embodiment identifies profilaggrin gene and protein. A profilaggrin gene comprises multiple filaggrin repeats, usually 10, 11 or 12 repeats. The filaggrin repeats are typically of the same length (972 bp, 324 amino acids in humans) as each other, although this is less typical of filaggrin repeats at the 5'- and 3'-ends of the mRNA. The filaggrin repeats may display considerable sequence variation, typically of from 0-50%, more typically of from 2-30%, yet more typically of from 10-15%, between repeats on the same allele and between different alleles. Usually variations are attributable to a single-base change but may also involve a change in charge (Gan et al (1990) Biochemistry, 29, 9432-9440). A consensus amino acid sequence map of a human filaggrin repeat is known (Gan et al (1990) Biochemistry, 29, 9432-9440) and preferably a filaggrin repeat will have at least 50%, more preferably at least 75%, more preferably 90%, yet more preferably at least 95% sequence identity to that consensus sequence or a variant of the consensus sequence shown in Gan et al (1990, Biochemistry, 29, 9432-9440). Normally the amino acid sequences encoding the amino and carboxy termini are more conserved, as are the 5' and 3' DNA sequences flanking the coding portions of the gene (Presland et al (1992) J Biol Chem, 267(33), 23772-23781). The presence of different profilaggrin alleles in the genome of an individual can be identified by methods well known in the art for distinguishing between macromolecules with divergent structures. The term "allele" as used herein with respect to profilaggrin refers to any profilaggrin gene comprising a polymorphism. In a preferred embodiment the term "allele" with respect to profilaggrin refers to a profilaggrin gene identifiable by the number of filaggrin repeats it encodes. However, the skilled person will appreciate that many other polymorphisms of the profilaggrin gene are possible and all profilaggrin alleles are included within the scope of the invention. For example, the different phenotypes observed between individuals having profilaggrin alleles encoding profilaggrin with 10, 11 or 12 filaggrin repeats may be a direct result of the differences in production of filaggrin. However, the skilled person will appreciate that the number of filaggrin repeats may instead be a 'marker' for some other sequence polymorphism in the different profilaggrin alleles, or in another gene within the epidermal differentiation complex. Thus the phenotype may not be directly related to the number of filaggrin repeats present. Thus it will be appreciated that methods described herein will be suitable to identify differences between any profilaggrin alleles and that the invention is not restricted to polymorphism in respect of the number of filaggrin repeats.

Typically an allele may be identified at the polynucleotide level, such as by analysis of genomic DNA or mRNA. The skilled person is well aware of methods for determining the presence or absence of different polynucleotides. Methods known for determining the presence or absence of particular RNA sequences include northern blots, reverse transcription and PCR (RT-PCR) and ribonuclease protection assays (Sambrook and Russell, (2001) Molecular Cloning: A Laboratory Manual. 3rd edition, Cold Spring Harbour Laboratory Press, New York, USA). Methods known for determining the presence or absence of particular DNA sequences include sequencing, Southern blots, PCR amplification of genomic DNA and analysis of restriction fragment length polymorphisms (RFLPs). See Sambrook and Russell (2001, Molecular Cloning: A Laboratory Manual. 3rd edition. Cold Spring Harbour Laboratory Press, New York, USA), Innis et al, (1995, PCR Strategies, Academic Press, Inc.: NY); Dieffenbach et al (1995, PCR Primer: A Laboratory Manual, New York: Cold Spring Harbor Press). DNA sequence analysis may also be achieved by detecting alteration in electrophoretic mobility of DNA fragments in gels with or without denaturing agents. Differences can also be visualized by high resolution gel electrophoresis or distinguished according to differences in DNA sequence melting points. See, e.g., Myers et al (1982, Science, 230, 1242). Methods for detecting the presence of specific sequences include detection techniques such as fluorescence-based detection methods, immune-based assays such as RIA, antibody staining such as Western blot analysis or in situ hybridization, using appropriately labeled probe.

Sequences useful for constructing probes suitable for use in detecting the presence of a sequence of interest include any nucleic acid sequence having at least about 50%, preferably at least 70%, more preferably at least 80% or greater sequence identity or homology with the sequence of a known profilaggrin gene or fragment thereof by a Blast search. "Percent (%) sequence identity" or "percent (%) sequence homology" is defined as the percentage of nucleic acid residues in a candidate sequence that are identical with the nucleic acid residues of the sequence of interest, after aligning the sequences and introducing gaps, if necessary to achieve maximum percent sequence identity, and not considering any conservative substitutions as part of the sequence identity. Methods for performing sequence alignment and determining sequence identity are known in the art, may be performed without undue experimentation, and calculations of % identity values may be obtained for example, using available computer programs such as WU-BLAST-2 (Altschul et al, 1996, Methods in Enzymology 266,460-480). One may optionally perform the alignment using set default parameters in the computer software program (Blast search, MacVector and Vector NTI). Based upon the restriction map of a particular allele, a banding pattern can be predicted when the Southern blot is hybridized with a probe which recognizes the sequence of interest. The level of stringency of hybridization used can vary depending upon the level of sensitivity desired, a particular probe characteristic, such as probe length and/or annealing temperature, or degree of homology between probe sequence and sequence of interest. Therefore, considerations of sensitivity and specificity will determine stringency of hybridization required for a particular assay.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperatures. The higher the degree of desired homology between the probe and hybridizable sequence, the higher the relative temperature that can be used. For additional details and explanation of stringency of hybridization reactions, see Ausubel et al (1995, Current Protocols in Molecular Biology, Wiley Interscience Publishers) or Protocols Online (URL: www.protocol-online.net/molbio/index.htm).

"Stringent conditions" or "high-stringency", as defined herein, may be identified by those that: (1) use low ionic strength and high temperature for washing, for example 0.1×SSC, 0.2% SDS at 65-70° C.

"Moderately-stringent conditions" may be identified as described by Sambrook and Russell (2001, Molecular Cloning: A Laboratory Manual, 3rd edition), and include the use of washing solution and hybridisation conditions (e.g. temperature, ionic strength, and % SDS) less stringent that those described above. An example of moderately stringent conditions is 0.2×SSC, 0.1% SDS at 58-65° C. The skilled artisan will recognise how to adjust temperature, ionic strength, etc. as necessary to accommodate factors such as probe length, degree of homology between probe and target site and the like. Therefore, in addition to the sequence of interest, it is contemplated that additional or alternative probe sequences which vary from that of the sequence of interest will also be useful in screening for the sequence of interest.

In a preferred embodiment profilaggrin alleles are identified by the number of filaggrin repeats present. Thus typically the method of identifying the profilaggrin alleles present in the genome of an individual comprises determining whether the alleles present have 10, 11 or 12 filaggrin repeats.

In one preferred embodiment allele identification is performed using PCR. Forward and reverse primers are prepared using techniques well known in the art and comprise a sequence based on an upstream region and a downstream region, respectively, relative to the sequence of the profilaggrin gene coding sequence encoding polymorphic filaggrin repeats. Preferably the upstream and downstream regions chosen for design of primers will be substantially conserved between different alleles. "Substantially conserved" includes within its meaning sequences having at least 50%, 60%, 70%, 80%, 90%. 95%, 98%, 99% or 100% sequence identity. Thus primers can be designed for binding to similar but non-identical sequences, for example by using degenerate primers or by including nucleotides that have a reduced specificity for the purposes of complementarity, such as inosine, within the primer. Preferably one, or more preferably both, of the forward and reverse primers are 100% identical to the upstream and/or downstream regions of each profilaggrin allele.

The PCR reaction is performed in order to amplify DNA obtained from the biological material from the sample taken from the individual. In one embodiment the DNA is genomic DNA extracted from the biological material. In another embodiment the DNA is cDNA which has been reverse transcribed from RNA, typically mRNA, which RNA has been extracted from the biological material. Methods for extracting genomic DNA, methods for extracting RNA, methods for extracting mRNA and methods for reverse transcription of RNA are well known in the art, for example see Sambrook and Russell (2001, Molecular Cloning: A Laboratory Manual. 3rd edition, Cold Spring Harbour Laboratory Press, New York, USA).

In a preferred embodiment the DNA is genomic DNA and the sample is a saliva sample or buccal swab. Methods for extracting DNA from saliva samples and buccal swabs are known in the art (Schie and Wilson (1997) Journal of Immunological Methods, 208, 91-101).

The PCR reaction can be performed under conditions well known in the art or as suggested by the manufacturer of a commercially available PCR kit. For example, amplification may be performed using from 0.1 to 30 sg/ml DNA substrate. Amplification may be performed using from 2 µM to 2 mM dNTPs. Amplification may be performed using from 2 µM to 2 mM forward and reverse primers. Amplification may be performed using and from 17 µM to 170 mM Mg2+. In a preferred embodiment amplification is performed using about 200 µM dNTPs. In a preferred embodiment amplification is performed using about 200 µM forward and reverse primers. In a preferred embodiment amplification is performed using about 1.7 mM Mg2+. By "about" is meant that the concentration used varies by no more than 50%. 25%, 10% or 5% from the concentration stated. Most preferably the PCR reaction is performed essentially as described in the exemplified methods below.

PCR products can then be analysed by any suitable method. Typically the PCR products are analysed by size fractionation, usually using gel electrophoresis performed in accordance with techniques well known in the art (see Sambrook and Russell (2001) Molecular Cloning: A Laboratory Manual. 3rd edition, Cold Spring Harbour Laboratory Press, New York, USA). Most preferably the PCR products are analysed essentially as described in the exemplified methods below.

Other methods suitable for identifying the profilaggrin alleles present in the genome of an individual include allele specific hybridisation; allele specific oligonucleotide hybridisation; and primer specific extension.

Allele specific hybridization uses probes overlapping a region of at least one profilaggrin allele and having about 5, 10, 20, 25 or 30 nucleotides around a polymorphic region. In a preferred embodiment, several probes capable of hybridizing specifically to other profilaggin alleles are attached to a solid phase support, e.g. a "chip," (which can hold up to about 250,000 oligonucleotides). Oligonucleotides can be bound to a solid support by a variety of processes, including lithography. Mutation detection analysis using these chips comprising oligonucleotides, also terms "DNA probe arrays" is described e.g., in Cronin et al (1996, Human Mutation 7, 244). In one embodiment, a chip comprises all the allelic variants of at least one polymorphic region of a profilaggrin gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain region (LCR), nested polymerase chain reaction, self sustained sequence replication (Guatelli et al (1990) Proc Natl Acad Sci USA 87, 1874-1878), transcriptional amplification system (Kwoh et al (1989) Proc Natl Acad Sci USA 86, 1173-1177), and Q-Beta Replicase (Lizardi (1988) Bio/Technology 6, 1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization % and the like.

In a merely illustrative embodiment a method of identifying profilaggrin alleles includes the steps of (i) isolating nucleic acid (e.g., genomic, RNA or both) from the cells of a sample collected from an individual (ii) contacting the nucleic acid sample with one or more primers which specifically hybridize 5' and 3' to at least one polymorphism in the profilaggrin allele under conditions such that hybridization and amplification of the polymorphic region of the allele occurs, and (iii) detecting the amplification product. These detection schemes are especially useful for the detection of nucleic acid molecules if such molecules are present in very low numbers.

An allele of profilaggrin may be identified by alterations in restriction enzyme cleavage patterns. For example, sample and control DNA is isolated, amplified (optionally) digested with one or more restriction endonucleases, and fragment length sizes are determined, for example by gel electrophoresis.

In yet another embodiment, any of a variety of sequencing reactions known in the art can be used to directly sequence the allele. Exemplary sequencing reactions include those based on techniques developed by Maxim and Gilbert (1997, Proc Natl Acad Sci USA 74, 560) or Sanger et al (1977, Proc Nat Acad Sci USA 74, 5463). It is also contemplated that any of a variety of automated sequencing procedures may be utilized when performing the subject assays (see, for example Biotechniques (1995) 19, 448), including sequencing by mass spectrometry (e.g. WO 94/16101; Cohen et al (1996) Adv Chromatogr 36, 127-162; and Griffin et al (1993) Appl Biochem Biotechnol 38, 147-159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

A profilaggrin allele may be identified by using cleavage agents (such as nuclease, hydroxylamine or osmium tetroxide and with piperidine) to detect mismatched bases in RNA/RNA or RNA/DNA or DNA/DNA heteroduplexes (Myers et al (1985) Science 230, 1242). In general, the art technique of "mismatch cleavage" starts by providing heteroduplexes formed by hybridizing (labeled) RNA or DNA containing the wild-type allele with a sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/RNA duplexes can be treated with hydroxylamine or osmium tetroxide and with piperidine in order to digest mismatched regions. After digestion of the mismatched regions, the resulting material is then separated by size, for example using denaturing polyacrylamide gel to determine the site of mutation. See, for example, Cotton et al (1988) Proc Natl Acad Sci USA 85, 4397; and Saleeba et al (1992) Methods Enzymol 217, 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) Carcinogenesis 15, 1657-1662). According to an exemplary embodiment, a probe based on a chosen profilaggrin allele is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

Examples of other techniques for detecting alleles include, but are not limited to, selective oligonucleotide hybridization, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al (1986) Nature 324, 163; Saiki et al (1989) Proc Natl Acad Sci USA 86, 6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

In another embodiment, identification of a profilaggrin allele may be carried out using an oligonucleotide ligation assay (OLA), as described, e.g., in U.S. Pat. No. 4,998,617 and in Landegren et al (1988. Science 241, 1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson et al have described a nucleic acid detection assay that combines attributes of PCR and OLA (Nickerson et al (1990) Proc Natl Acad Sci USA 87, 8923-27). In this method, PCR is used to achieve the exponential amplification of target DNA, which is then detected using OLA.

Several techniques based on this OLA method have been developed and can be used to detect profilaggrin alleles. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al (1997, Nucleic Acids Res 24, 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colours.

Once the profilaggrin genotype of an individual has been determined, that individual can be categorised as having a high or low predisposition to a skin condition. Thus methods of the invention can be used to identify the profilaggrin genotype of an individual in order to determine that individual's predisposition to a skin condition. Accordingly the invention provides a system for determining the predisposition of an individual to a skin condition comprising means for identifying the profilaggrin alleles present in the genome of a sample taken from the individual.

The invention also provides for the use of a primer of the invention in a method of determining the predisposition of an individual to a skin condition as described above. Thus kits and assay components comprising PCR primers and oligonucleotides for hybridisation as described above form further aspects of the invention.

The primer kit of the present invention is useful for identifying profilaggrin alleles using the polymerase chain reaction. The kit comprises a set of pairs of single stranded DNA primers which can be annealed to sequences flanking the polymorphism and within or surrounding the profilaggrin gene on the relevant chromosome in order to prime amplifying DNA synthesis of the gene itself. The complete set may allow synthesis of all of the nucleotides of the profilaggrin allele coding sequences, ie the exons, or may allow synthesis of less than the entire coding region. The set of primers preferably allows synthesis of both intron and exon sequences, as allelic variations may be found in a profilaggrin gene intron. The kit can also contain DNA polymerase, preferably a thermophilic DNA polymerase, more preferably Taq polymerase, yet more preferably Elongase (GIBCOBRL Life Technologies) and suitable reaction buffers. Such components are known in the art.

Having the ability to look at a patient on an individual basis will allow for a more accurate diagnosis and specific treatment plan. Genotyping is the process of obtaining an individual's DNA sequence by using biological assays. By having a detailed account of an individual's DNA sequence, their genome can then be compared to a reference genome, like that of the Human Genome Project, to assess the existing genetic variations that can account for possible diseases. An individual's genetic make-up also plays a large role in how well they respond to a certain treatment, and therefore, knowing their genetic content can change the type of treatment they receive. The system applies pharmacogenomics by using an individual's genome to provide a more informed and tailored cosmetic material prescription. Often, cosmetic materials are prescribed with the idea that it will work relatively the same for everyone, but in the application of cosmetic materials, there are a number of factors that must be considered. The detailed account of genetic information from the individual will help prevent adverse events, allow for appropriate dosages, and create maximum efficacy with cosmetic material prescriptions. The pharmacogenomic process for discovery of genetic variants that predict adverse events to a specific cosmetic material has been termed toxgnostics.

In addition to specific treatment, personalized medicine can greatly aid the advancements of preventive care. For instance, many women are already being genotyped for certain mutations in the BRCA1 and BRCA2 gene if they are predisposed because of a family history of breast cancer or ovarian cancer. As more causes of diseases are mapped out according to mutations that exist within a genome, the easier they can be identified in an individual. Measures can then be taken to prevent a disease from developing. Even if mutations were found within a genome, having the details of their DNA can reduce the impact or delay the onset of certain diseases. Having the genetic content of an individual will allow better guided decisions in determining the source of the disease and thus treating it or preventing its progression. This will be extremely useful for diseases like Alzheimer's or cancers that are thought to be linked to certain mutations in human DNA.

The system can be used to test efficacy and safety of a cosmetic material specific to a targeted patient group/subgroup is companion diagnostics. This technology is an assay that is developed during or after a cosmetic material is made available on the market and is helpful in enhancing the therapeutic treatment available based on the individual. These companion diagnostics have incorporated the pharmacogenomic information related to the cosmetic material into their prescription label in an effort to assist in making the most optimal treatment decision possible for the patient.

Having an individual's genomic information can be significant in the process of developing cosmetic materials as they await approval from the FDA for public use. Having a detailed account of an individual's genetic make-up can be a major asset in deciding if a patient can be chosen for inclusion or exclusion in the final stages of a clinical trial Being able to identify patients who will benefit most from a clinical trial will increase the safety of patients from adverse outcomes caused by the product in testing, and will allow smaller and faster trials that lead to lower overall costs. In addition, cosmetic materials that are deemed ineffective for the larger population can gain approval by the FDA by using personal genomes to qualify the effectiveness and need for that specific cosmetic material or therapy even though it may only be needed by a small percentage of the population. Treatments can be more specifically tailored to an individual and give insight into how their body will respond to the cosmetic material and if that cosmetic material will work based on their genome. The personal genotype can allow physicians to have more detailed information that will guide them in their decision in treatment prescriptions, which will be more cost-effective and accurate.

The system next generates gene-environmental factor interactions to help lifestyle recommendations. The system creates a matrix that correlates gene and environmental impacts. One embodiment generates gene based cosmetic material-cosmetic material interactions that allow the physician or pharmacist to avoid health problems for the patient. FIG. 3 shows a method 300 for predicting cosmetic material-cosmetic material interactions based on genetic data and clinical side effects, in accordance with an embodiment of the present principles. The process includes the following: At 310, construct a comprehensive gene-cosmetic material-cosmetic material interactions (GDDIs) training dataset that includes all pharmaceutical, pharmacokinetic (PK), pharmacogenetic (PG), and pharmacodynamic (PD) GDDIs from multiple data sources for each cosmetic material in a set of cosmetic materials under consideration. In an embodiment, the multiple data sources can include, but are not limited to, the following: gene sequencers, clinical trials; cosmetic material development information; empirical information; a cosmetic material bank; cosmetic material label information; an adverse event reporting system (e.g., the FDA Adverse Event Reporting System information (FAERS)); and text mining from scientific documents (e.g., search tool for interactions of chemicals (STITCH)). At step 320, construct side effect features for each of the cosmetic materials in the set from genetic panels for an individual and side effects associated with the cosmetic materials in the set. In an embodiment, the genetic panels are generated by genetic sequencers, and all cosmetic materials' side effects, from which the side effect features are constructed, come from one or more of the following sources: clinical trials; cosmetic material development; empirical information; FDA cosmetic material label (SIDER and DAILYMED®); FDA Adverse Event Reporting System (FAERS); and real-world evidence. At 330, build, using the GDDIs training dataset, a GDDIs classifier for predicting whether or not a given cosmetic material pair derived from the set of cosmetic materials results in adverse interactions, and repeat this process for all possible cosmetic material pairs derivable from the set of cosmetic materials. In an embodiment, the features used for building the classifier can include, but are not limited to, the following: cosmetic material's clinical side effect keywords; and other cosmetic material properties (e.g., chemical structures, protein targets, and so forth).

At 340, obtain predicted GDDIs from the classifier. At 350, for each side effect, perform statistical test to determine whether that side effect is differentially shown between positive predicted GDDIs and negative predicted GDDIs. In one embodiment, the term "positive predicted GDDIs" refers to cosmetic materials pairs that cannot be taken together given a patient genetic profile. In contrast, the term "negative predicted GDDIs" refers to cosmetic materials pairs that may be safe to use together with a genetic profile.

Side effects are effects after taking a medicine, which are other than the intended therapeutic effects. Label side effects means the side effects are recorded in cosmetic material labels (for example, but not limited to, SIDER database, DAILYMED®, and so forth). FDA side effects means the side effects are recorded in, for example, but not limited to, the FDA Adverse Event Reporting System (FAERS). Consider, for example, the cosmetic material Ibuprofen as an example, DAILYMED®, records its 249 types of label side effects (e.g., abdominal discomfort, confusion, dry mouth, vomiting, and weight loss), and FAERS records its 728 types of FDA side effects (e.g., anxiety, ear ache, fatigue, tooth loss, sleep disorder).

In 380, relative interactions between the different cosmetic material substances can be determined by locating references in the interaction data for each of the cosmetic material substances to others of the substances. Finally, in block 390, the relative interactions can be rendered within a report such as a paper report or a graphical user interface display. Optionally, an activatable link can be provided in the display for selected ones of the cosmetic material substances for reordering the selected ones of the cosmetic material substances. In this way, the relative cosmetic material interactions resulting from the dispensing of multiple different cosmetic material substances based on patient genetic data can be determined without requiring a tedious manual process of looking up cosmetic material interaction data for each substance and manually correlating the cosmetic material interaction data for the specific combination of dispensed substances.

The system can also perform GDDI discovery and prediction that uses molecular structure similarity information derived from fingerprint-based modeling. Identifying new GDDIs using structural similarity is based on the basic idea that if cosmetic material A interacts with cosmetic material B, and cosmetic material C is structurally similar to A, then C should also interact with B (the argument also follows if A is replaced with B). Hence, by combining knowledge of known interactions with structural similarity it is possible to identify new interactions. The process uses a list of cosmetic material-cosmetic material interactions from Cosmetic materialBank (step 1), structural similarity computation was carried out using molecular fingerprints (step 2), apply gene-cosmetic material interaction to similar cosmetic materials, and a new list of gene-cosmetic material interactions can be inferred.

Structural similarity can be identified in three steps: 1) Collecting and processing cosmetic material structures: Information on the structures of the compounds in Cosmetic materialBank is retrieved along with the SMILE code (a chemical notation representing a chemical structure in linear textual form). 2) Structural representation: BIT_MACCS (MACCS Structural Keys Bit packed) fingerprints are calculated for all molecules included in the study and each molecule is represented as a bit vector that codes the presence or absence of structural features where each feature is assigned a specific bit position. 3) Similarity measures, computation, and data representation: Different measures are used to compare similarity between two molecular fingerprints. In one embodiment, the molecular fingerprints were compared using Tanimoto coefficient (TC). The TC can span values between 0 and 1, where 0 means 'maximum dissimilarity' and 1 means 'maximum similarity.' The TC between two fingerprint representations A and B is defined as the number of features present in the intersection of both fingerprints A and B divided by the number of features present in the union of both fingerprints. Next, for each cosmetic material affected by a particular gene, the process predicts new gene based DDIs. One embodiment predicts new DDIs reduces to matrix multiplication of the matrices M1, which consists of the established interactions, and M2, which consists of the similarity matrix.

The pharmacogenomic information can be applied to cosmetic material labeling. One embodiment may contain information on genomic biomarkers and can describe:

Cosmetic material exposure and clinical response variability

Risk for adverse events

Genotype-specific dosing

Mechanisms of cosmetic material action

Polymorphic cosmetic material target and disposition genes

The information may include specific actions to be taken based on the biomarker information. Pharmacogenomic information can appear in different sections of the labeling depending on the actions. Biomarkers in the table include but are not limited to germ-line or somatic gene variants, functional deficiencies, expression changes, and chromosomal abnormalities; selected protein biomarkers that are used to select patients for treatment are also included.

In one embodiment, the process includes constructing a gene-cosmetic material interactions training dataset that includes pharmaceutical, pharmacokinetic or pharmacodynamics, and pharmacogenomics cosmetic material-cosmetic material interactions for each cosmetic material; constructing side effect features for each of the plurality of cosmetic materials from side effects associated with the plurality of cosmetic materials; running a gene-cosmetic material-cosmetic material interactions classifier that predicts adverse cosmetic material-cosmetic material interactions for cosmetic material pairs and the genetic scan; and for each of the side effects, performing a Fisher's exact test to determine predicted gene-cosmetic material-cosmetic material interactions. Fisher's exact testis a statistical significance test used in the analysis of contingency tables. It is one of a class of exact tests, so called because the significance of the deviation from a null hypothesis (e.g., P-value) can be calculated exactly, rather than relying on an approximation that becomes exact in the limit as the sample size grows to infinity, as with many statistical tests.

Figure 4:
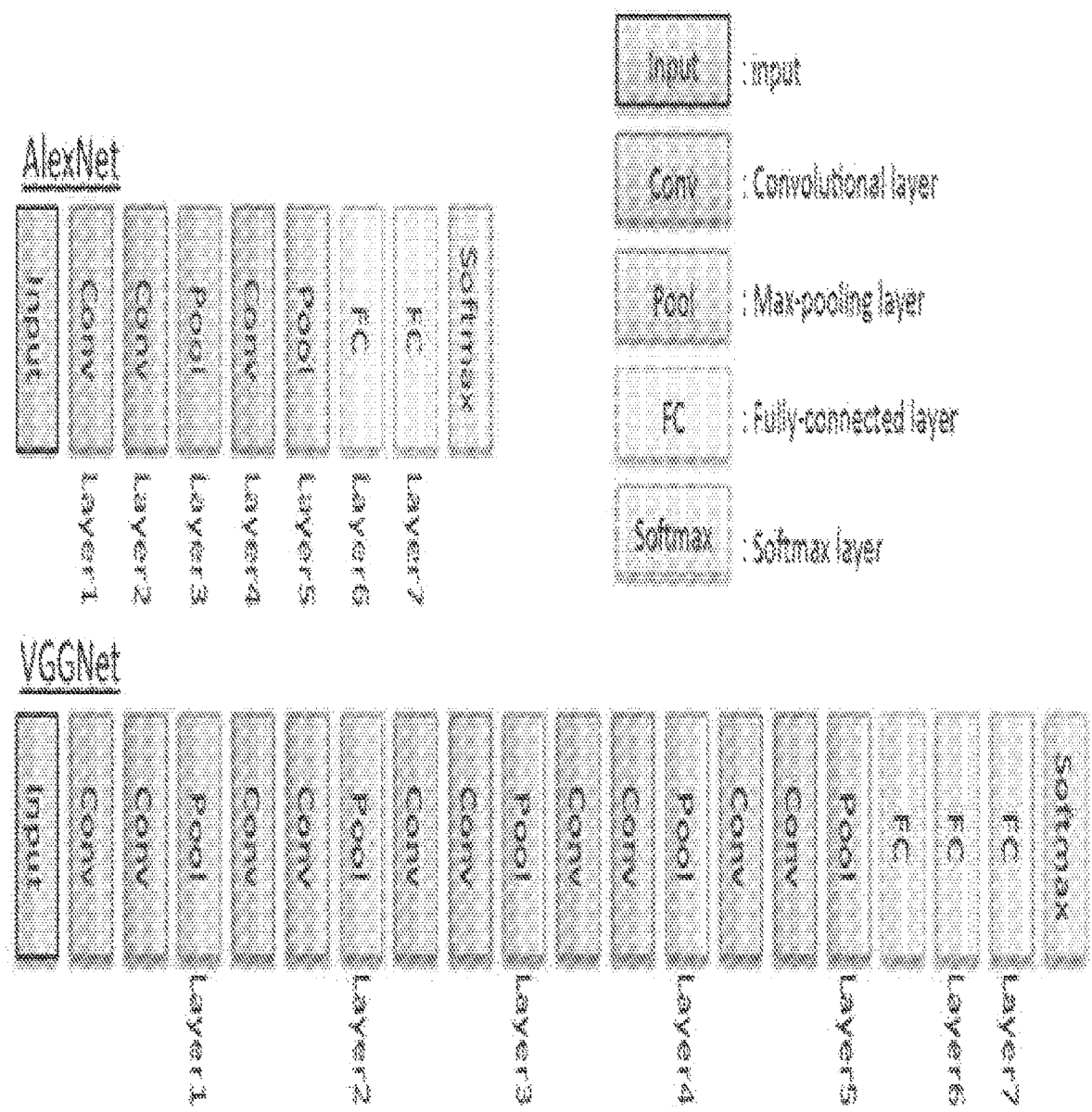
FIG. 4 shows a big data learning machine to process genetic data and determine pharmacogenetics relationship among genes and cosmetic materials for cosmetic material interaction purposes.

FIG. 4 shows a deep learning machine using deep convolutionary neural networks for detecting genetic based cosmetic material-cosmetic material interaction. One embodiment uses an AlexNet: 8-layer architecture, while another embodiment uses a VGGNet: 16-layer architecture (each pooling layer and last 2 FC layers are applied as feature vector). For cosmetic materials, the indications of use and other cosmetic materials used capture most of many important covariates. One embodiment access data from SIDER (a text-mined database of cosmetic material package inserts), the Offsides database that contains information complementary to that found in SIDER and improves the prediction of protein targets and cosmetic material indications, and the Twosides database of mined putative DDIs also lists predicted adverse events, all available at the http://PharmGKB.org Web site.

The system of FIG. 4 receives data on adverse events strongly associated with indications for which the indication and the adverse event have a known causative relationship. A cosmetic material-event association is synthetic if it has a tight reporting correlation with the indication (p≥0.1) and a high relative reporting (RR) association score (RR≥2). Cosmetic materials reported frequently with these indications were 80.0 (95% CI, 14.2 to 3132.8; P<0.0001, Fisher's exact test) times as likely to have synthetic associations with indication events. Disease indications are a significant source of synthetic associations. The more disproportionately a cosmetic material is reported with an indication (x axis), the more likely that cosmetic material will be synthetically associated. For example, adverse events strongly associated with cosmetic materials are retrieved from the cosmetic material's package insert. These cosmetic material-event pairs represent a set of known strong positive associations.

Adverse events related to sex and race are also analyzed. For example, for physiological reasons, certain events predominantly occur in males (for example, penile swelling and azoospermia). Cosmetic materials that are disproportionately reported as causing adverse events in males were more likely to be synthetically associated with these events. Similarly, adverse events that predominantly occur in either relatively young or relatively old patients are analyzed.

"Off-label" adverse event data is also analyzed, and off-label uses refer to any cosmetic material effect not already listed on the cosmetic material's package insert. For example, the SIDER database, extracted from cosmetic material package inserts, lists 48,577 cosmetic material-event associations for 620 cosmetic materials and 1092 adverse events that are also covered by the data mining. Offsides recovers 38.8% (18,842 cosmetic material-event associations) of SIDER associations from the adverse event reports. Thus, Offsides finds different associations from those reported during clinical trials before cosmetic material approval.

Polypharmacy side effects for pairs of cosmetic materials (Twosides) are also analyzed. These associations are limited to only those that cannot be clearly attributed to either cosmetic material alone (that is, those associations covered in Offsides). The database contains an significant associations for which the cosmetic material pair has a higher side-effect association score, determined using the proportional reporting ratio (PRR), than those of the individual cosmetic materials alone. The system determines pairwise similarity metrics between all cosmetic materials in the Offsides and SIDER databases. The system can predict shared protein targets using cosmetic material-effect similarities. The side-effect similarity score between two cosmetic materials is linearly related to the number of targets that those cosmetic materials share.

The system can determine relationships between the proportion of shared indications between a pair of cosmetic materials and the similarity of their side-effect profiles in Offsides. The system can use side-effect profiles to suggest new uses for old cosmetic materials. While the preferred system predicts existing therapeutic indications of known cosmetic materials, the system can recommend cosmetic material repurposing using cosmetic material-effect similarities in Offsides.

Corroboration of class-wide interaction effects with EMRs. The system can identify DDIs shared by an entire cosmetic material class. The class-class interaction analysis generates putative cosmetic material class interactions. The system analyzes laboratory reports commonly recorded in EMRs that may be used as markers of these class-specific DDIs.

The system can be used systematic cosmetic material surveillance. The FDA manages a collection of adverse cosmetic material event reports to monitor the safety of cosmetic materials. They rely on physicians, pharmaceutical companies, and patients to volunteer these reports. Since reporting is not mandatory, many adverse cosmetic material events that occur are never reported to the FDA. To address this issue, an embodiment of the present invention uses an algorithm to infer unreported adverse cosmetic material events. This embodiment relies on the fact that many adverse events occur together. For example, nausea and vomiting commonly manifest together. Therefore, if a cosmetic material is observed to causes nausea, it can be inferred that it also causes vomiting.

The successful prediction of side effects before a cosmetic material enters clinical trials can be done. Chemical informatics techniques can predict cosmetic material side effects by comparing the structural similarity of cosmetic materials. Protein structural similarity is learned by the deep learning system to predict cosmetic material side effects. More recently, network and chemical properties are used for predictive models of cosmetic material effects and leverage the system's comprehensive database of known cosmetic material effects.

In another aspect, a method for analyzing a disease state of a subject includes capturing a first liquid biopsy from the subject; providing the liquid biopsy to a genetic analyzer to identify the subject's genetic information of a first disease state at a first time point; searching for genetically similar patients and predicting a mutation of the disease into a second disease state at a second time point; analyzing a treatment database and recommending a treatment given the first and second disease states; capturing a second liquid biopsy from the subject at a second time point; providing the second liquid biopsy to the genetic analyzer to identify the subject's genetic information; and if the genetic information from the second time point matches the predicted mutation, continuing the recommended treatment for the subject and otherwise changing the recommended treatment.

In yet another aspect, a method to detect abnormal cellular activities includes sequencing of cell-free nucleic acid with a genetic analyzer or a DNA sequencer; comparing current sequence reads with prior sequence reads from at least two time points; detecting a mutation of the cell-free nucleic acid and updating a diagnostic confidence indication accordingly; and detecting the presence or absence of genetic alteration and/or amount of genetic variation in an individual based on the diagnostic confidence indication of the sequence read.

In a further aspect, a method for analyzing a disease state of a subject includes capturing a first liquid biopsy from the subject; providing the liquid biopsy to a genetic analyzer to identify the subject's genetic information of a first disease state at a first time point; searching for genetically similar subject profiles and predicting a mutation of the disease into a second disease state at a second time point; capturing a second liquid biopsy from the subject; providing the second liquid biopsy to a genetic analyzer to identify the subject's genetic information at a second time point; and if the genetic information from the second time point matches the predicted mutation, continuing the recommended treatment for the subject and otherwise changing the recommended treatment.

In another aspect disclosed herein is a method for analyzing a disease state of a subject by characterizing the subject's genetic information at two or more time points with a genetic analyzer, e.g., a DNA sequencer; and using the information from the two or more time points to produce an adjusted test result in the characterization of the subject's genetic information.

In another aspect, a method detects a trend in the amount of mutation cancer polynucleotides in a sample from a subject over time by determining a frequency of the cancer polynucleotides at a plurality of time points; determining an error range for the frequency at each of the plurality of time points; determining, between an earlier and later time point, whether error ranges (1) overlap, indicating stability of frequency, (2) an increase at the later time point outside the error range, indicating increase in frequency or (3) a decrease at the later time point outside the error range, indicating decrease in frequency.

In yet another aspect, a method detects mutation cellular activities by sequencing of cell-free nucleic acid with a genetic analyzer, e.g., a DNA sequencer; comparing later (e.g., current) sequence reads with prior sequence reads from at least two time points and updating a diagnostic confidence indication accordingly; and detecting the presence or absence of genetic alteration and/or amount of genetic variation in an individual based on the diagnostic confidence indication of the sequence read. A genetic analyzer includes any system for genetic analysis, e.g., by sequencing (DNA sequencer) or hybridization (microarray, fluorescent in situ hybridization, bionanogenomics) or other.

In another aspect, a method detects a mutation in a cell-free or substantially cell free sample obtained from a subject by generating consensus sequences by comparing later (e.g., current) sequence reads by a genetic analyzer, e.g., a DNA sequencer, with prior sequence reads from a prior period and updating a diagnostic confidence indication based on the prior sequence reads, each consensus sequence corresponding to a unique polynucleotide among a set of tagged parent polynucleotides, and generating a genetic profile of extracellular polynucleotides in the subject, wherein the genetic profile comprises a plurality of data resulting from copy number variation or mutation analyses.

In another aspect disclosed herein is a method to detect mutation cellular activities by providing at least one set of tagged parent polynucleotides, and for each set of tagged parent polynucleotides; amplifying the tagged parent polynucleotides in the set to produce a corresponding set of amplified progeny polynucleotides; with a genetic analyzer, e.g., a DNA sequencer, sequencing a subset of the set of amplified progeny polynucleotides, to produce a set of sequencing reads; and collapsing the set of sequencing reads to generate a set of consensus sequences by comparing current sequence reads with prior sequence reads from at least one prior period and updating diagnostic confidence indication accordingly, each consensus sequence corresponding to a unique polynucleotide among the set of tagged parent polynucleotides.

In yet another aspect, a method detects a mutation in a cell-free or substantially cell free sample obtained from a subject by sequencing extracellular polynucleotides from a bodily sample from a subject with a genetic analyzer, e.g., a DNA sequencer; for each of the extracellular polynucleotide, generating a plurality of sequencing reads; filtering out reads that fail to meet a set threshold; mapping sequence reads derived from the sequencing onto a reference sequence; identifying a subset of mapped sequence reads that align with a variant of the reference sequence at each mappable base position; for each mappable base position, calculating a ratio of (a) a number of mapped sequence reads that include a variant as compared to the reference sequence, to (b) a number of total sequence reads for each mappable base position; and comparing current sequence reads with prior sequence reads from at least on other time point and updating a diagnostic confidence indication accordingly.

The method identifies one or more evolutionary paths of escape and evolved tumor treatment(s). These paths are caused by various drivers. For example, as shown in FIG. 5A, common aberrations in cancer genomes can lead to the abnormal chromosome numbers (aneuploidy) and chromosome structures of a cancer genome. In FIG. 5A, lines indicate the genome with germline genome on top and cancer genome with somatic aberrations below. Double lines are used when differentiating heterozygous and homozygous changes is useful. Dots represent single nucleotide changes, whereas lines and arrows represent structural changes.

Figure 5B:
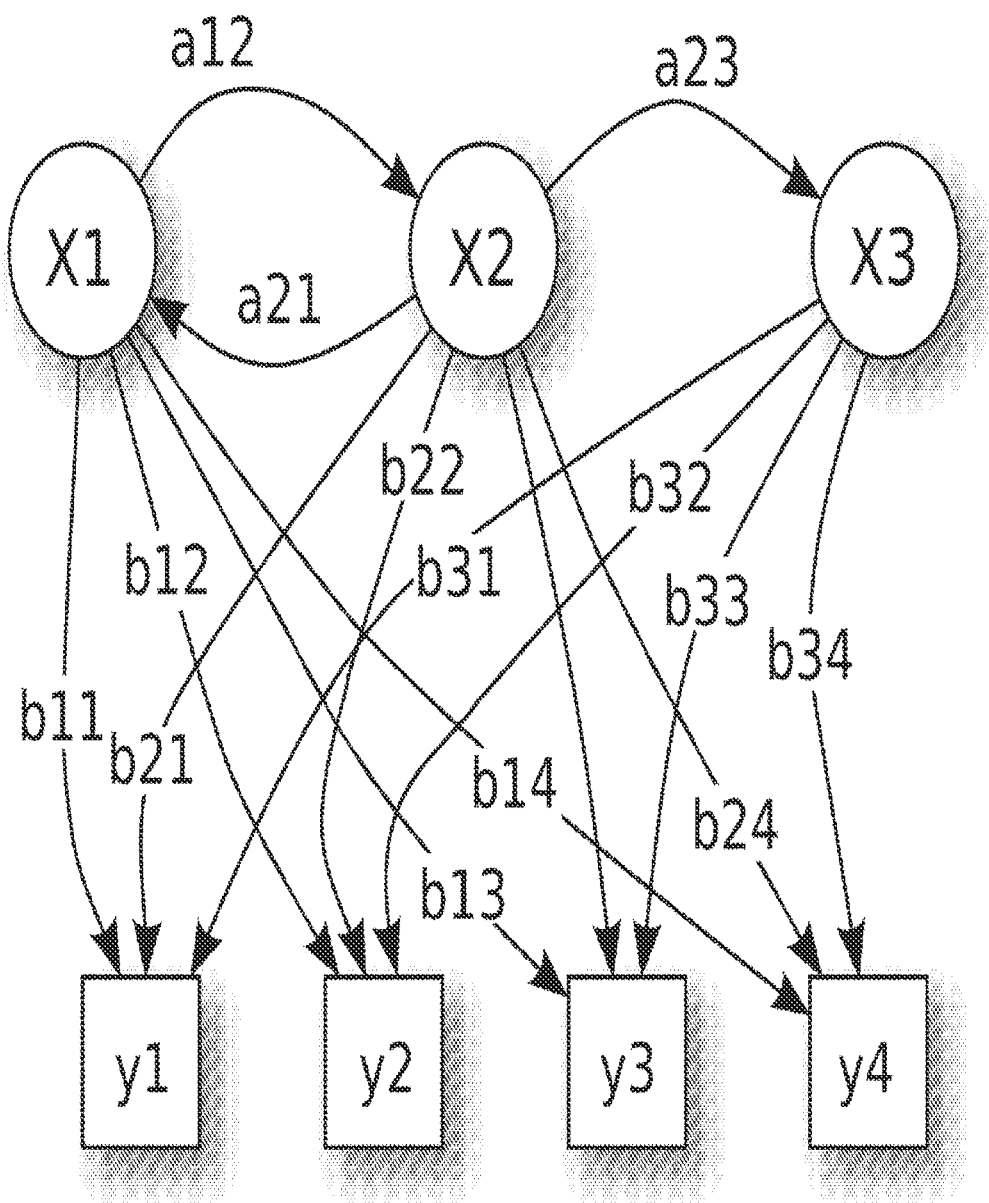
FIG. 5B shows an exemplary system to detect the evolutionary paths of escape.

FIG. 5B shows an exemplary system to detect the evolutionary paths of escape for skin cancer. The system can be a Hidden Markov model (HMM), which is is a statistical Markov model in which the system being modeled is assumed to be a Markov process with unobserved (hidden) states. As known to those skilled in the art, an HMM can be presented as the simplest dynamic Bayesian network. In simpler Markov models (like a Markov chain), the state is directly visible to the observer, and therefore the state transition probabilities are the only parameters. In a hidden Markov model, the state is not directly visible, but output, dependent on the state, is visible. Each state has a probability distribution over the possible output tokens. Therefore the sequence of tokens generated by an HMM gives some information about the sequence of states. A hidden Markov model can be considered a generalization of a mixture model where the hidden variables (or latent variables), which control the mixture component to be selected for each observation, are related through a Markov process rather than independent of each other. As shown in FIG. 5B, the HMM is typically defined by a set of hidden states, a matrix of state transition probabilities and a matrix of emission probabilities. Each hidden state has different statistical properties.

Mutations and genetic alterations including in copy number, for example, allelic imbalances, chromosomal copy number changes, such as amplifications, deletions, aneuploidy, loss of heterozygosity, and micro-satellite instability are often found to be associated with a disease state, for example, cancer. It has been observed that alterations in chromosomal copy number and loss of heterozygosity (LOH) are forms of genetic changes that often signal the activation of oncogenes and inactivation of tumor suppressor genes (anti-oncogenes). Variations in the form of copy number polymorphisms (CNP) can also occur in normal individuals.

Identification of the loci implicated in these aberrations can generate anchor points which facilitate oncogenomics and toxicogenomics studies. Subsequently the shared LOH and aberrant CN regions can be used to partition the transcriptome data and track the differential transcript expression in the affected genomic segments. Locating and exploring such alteration events is an important research approach toward understanding the cause and progression of disease. For diploid organisms, the abnormal chromosomal state results when the normal diploid distribution is perturbed, resulting in changes that can include, for example, deletions, amplifications and translocations. Deletions can be of a partial chromosome ranging from micro-deletions on the order of several kb to macro-deletions of mega bases, entire arms of a chromosome or entire chromosomes. Amplifications can range from partial chromosomal amplifications to gains of a single copy of a chromosome to multiple copy gains of one or more chromosomes. Translocations generally comprise parts of a first chromosome being translocated to another chromosome.

FIG. 5B shows the general architecture of an instantiated HMM for mutation detection. Each oval shape X1, X2, X3 represents a random variable that can adopt any of a number of values. The random variable x(t) is the hidden state at time t(x(t) ∈ {x1, x2, x3}). The random variable y(t) is the observation at time t (with y(t) ∈ {y1, y2, y3, y4}). The arrows in the diagram (often called a trellis diagram) denote conditional dependencies. The conditional probability distribution of the hidden variable x(t) at time t, given the values of the hidden variable x at all times, depends only on the value of the hidden variablex(t−1): the values at time t−2 and before have no influence. This is called the Markov property. Similarly, the value of the observed variable y(t) representing the mutation conditions only depends on the value of the hidden variable x(t) (both at timet).

In FIG. 5B, the state space of the hidden variables is discrete, while the observations themselves can either be discrete (typically generated from a categorical distribution) or continuous (typically from a Gaussian distribution). The parameters of a hidden Markov model are of two types, transition probabilities and emission probabilities (also known as output probabilities). The transition probabilities control the way the hidden state at time is chosen given the hidden state at time. The hidden state space is assumed to consist of one of possible values, modeled as a categorical distribution. (See the section below on extensions for other possibilities.) This means that for each of the possible states that a hidden variable at time can be in, there is a transition probability from this state to each of the possible states of the hidden variable at time, for a total of transition probabilities. Note that the set of transition probabilities for transitions from any given state must sum to 1. Thus, the matrix of transition probabilities is a Markov matrix. Because any one transition probability can be determined once the others are known, there are a total of transition parameters.

In addition, for each of the possible states, there is a set of emission probabilities governing the distribution of the observed variable at a particular time given the state of the hidden variable at that time. The size of this set depends on the nature of the observed variable. For example, if the observed variable is discrete with possible values, governed by a categorical distribution, there will be separate parameters, for a total of emission parameters over all hidden states. On the other hand, if the observed variable is an -dimensional vector distributed according to an arbitrary multivariate Gaussian distribution, there will be parameters controlling the means and parameters controlling the covariance matrix, for a total of emission parameters. (In such a case, unless the value of is small, it may be more practical to restrict the nature of the covariances between individual elements of the observation vector, e.g. by assuming that the elements are independent of each other, or less restrictively, are independent of all but a fixed number of adjacent elements).

The HMM method can model a somatic evolution of cancer. The method includes modeling genetic instability, which results in abnormal numbers of chromosomes or aneuploidy, elevated mutation rates, and altered distributions of mutational patterns.

The method can identify one or more cancer mutation drivers. These drivers include those that disrupt cellular signaling pathways essential for multicellular organisms and possible mutations that increase somatic fitness of cancer cells. The method can include identifying dynamics of tumor progression in a population based on interactions with an environment. The method includes collecting repeated genetic observations to enhance statistical inference about the evolution of tumors.

The method includes recommending or providing a therapeutic regimen in anticipation of the one or more escape paths. Diagnosis of cancer can be done by analyzing the genetic variants, even in the presence of noise. The analysis can be based on the frequency of Sequence Variants or Level of CNV and a diagnosis confidence indication or level for detecting genetic variants in the noise range can be established. The process increases the diagnosis confidence using a plurality of measurements to increase confidence of Diagnosis (6), or alternatively using measurements at a plurality of time points to determine whether cancer is advancing, in remission or stabilized. The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants. The relative amount of tumor polynucleotides in a sample of cell free polynucleotides is referred to as the "tumor burden." Measurements of a parameter, whether or not they are in the noise range, may be provided with a confidence interval. Tested over time, one can determine whether a cancer is advancing, stabilized or in remission by comparing confidence intervals over time. Where the confidence intervals do not overlap, this indicates the direction of disease.

In one implementation, using measurements from a plurality of samples collected substantially at once or over a plurality of time points, the diagnostic confidence indication for each variant can be adjusted to indicate a confidence of predicting the observation of the CNV or mutation. The confidence can be increased by using measurements at a plurality of time points to determine whether cancer is advancing, in remission or stabilized. The diagnostic confidence indication can be assigned by any of a number of known statistical methods is assigned and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two time points can be separated by about a month to about a year, about a year to about 5 years, or no more than about three months.

The HMM detect with high sensitivity genetic variation in a sample of initial genetic material. The methods involve using one to three of the following tools: First, the efficient conversion of individual polynucleotides in a sample of initial genetic material into sequence-ready tagged parent polynucleotides, so as to increase the probability that individual polynucleotides in a sample of initial genetic material will be represented in a sequence-ready sample. This can produce sequence information about more polynucleotides in the initial sample. Second, high yield generation of consensus sequences for tagged parent polynucleotides by high rate sampling of progeny polynucleotides amplified from the tagged parent polynucleotides, and collapsing of generated sequence reads into consensus sequences representing sequences of parent tagged polynucleotides. This can reduce noise introduced by amplification bias and/or sequencing errors, and can increase sensitivity of detection. Third, the noise in the detection of mutations and copy number variations is reduced by comparing prior sample analysis with the current sample and increasing a diagnostic confidence indication if the same mutations and copy number variations have appeared in prior analysis and otherwise decreasing the diagnostic confidence indication if this is the first time the sequence is observed.

Figure 5C:
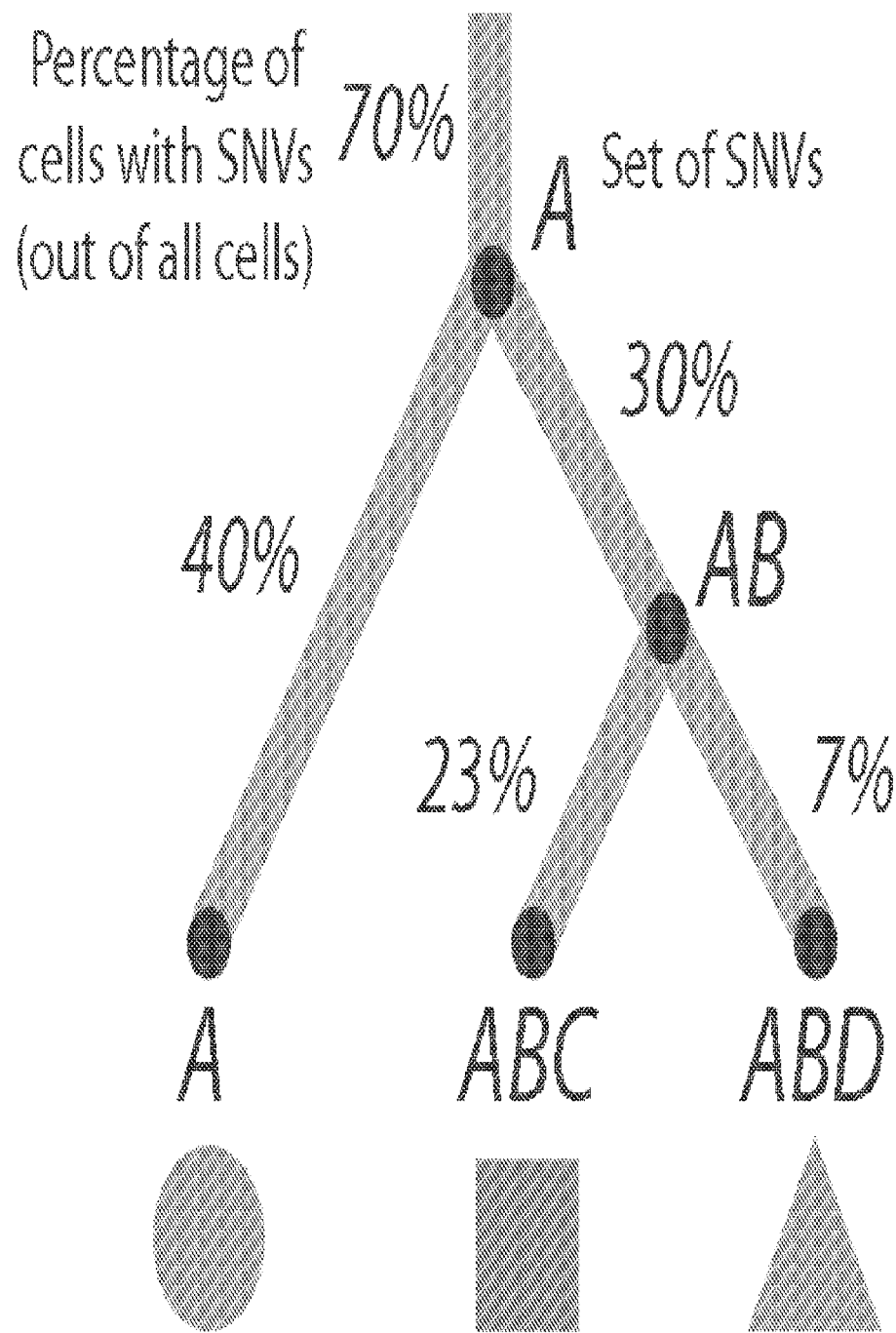
FIG. 5C shows an exemplary model generated by the system of FIG. 5B.

FIG. 5C shows an exemplary model generated by the system of FIG. 2B for inferring tumor phylogeny from next-generation sequencing data. The subclones are related to each other by an evolutionary process of acquisition of mutations. In this example, the three clones (leaf nodes) are characterized by different combinations of the four single nucleotide variant (SNV) sets A, B, C, and D. The percentages on the edges of the tree indicate the fraction of cells with this particular set of SNVs, e.g., 70% of all cells carry A, 40% additionally carry B, and only 7% carry A, B, and D.

Figure 5D:
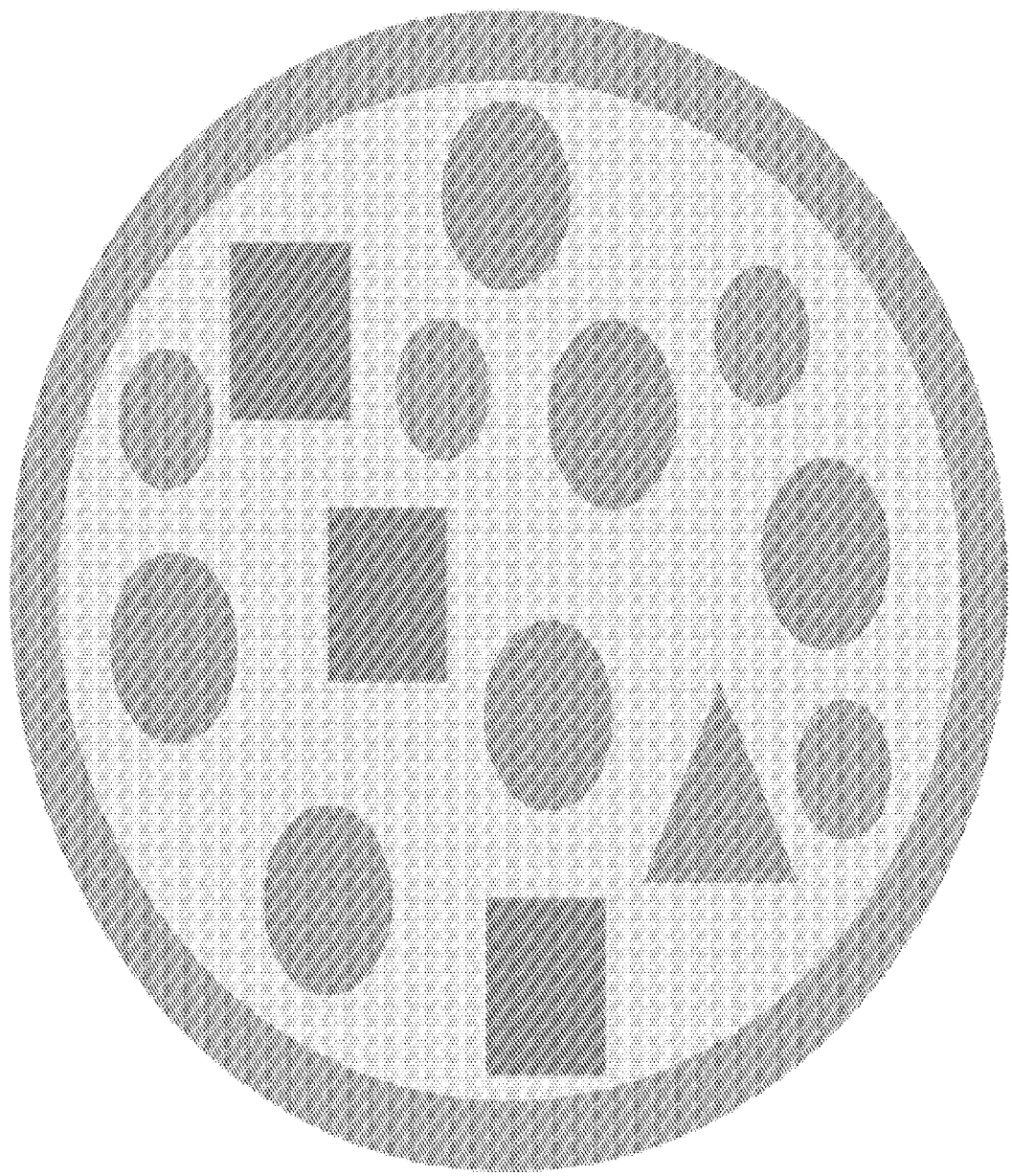
FIG. 5D shows an exemplary a heterogeneous collection of normal cells and skin cancer subclones developed during an evolutionary history of a tumor.

FIG. 5D shows an exemplary a heterogeneous collection of normal cells and cancer subclones developed during an evolutionary history of a tumor. The evolutionary history of a tumor gives rise to a heterogeneous collection of normal cells (small discs) and cancer subclones (large discs, triangles, squares). Internal nodes that have been fully replaced by their descendants (like the one carrying SNV sets A and B without C or D) are no longer part of the tumor.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

For the purposes of this description, a computer-usable or computer readable medium can be any apparatus that can contain, store, communicate, or transport the program for use by or in connection with the instruction execution system, apparatus, or device. The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

The pattern recognizer can identify beauty trends derived from Google's search data. Trends is a numeric/historic representation of the relative volume of searches made on Google. It creates indexes that show trending instead of actual volume (a big difference between Trends and Keyword Planner); this data can be mined for actionable insights you just can't get from Keyword Planner. The results are broken out into two separate graphs: historic trending (interest over time) and localized (regional) behavior. Trending Stories rely on technology from the Knowledge Graph across Google Search, Google News, and YouTube to detect when topics are trending on these three platforms. The Knowledge Graph enables the system to connect beauty trends with real-world things and places. The algorithm for trending stories groups topics together that are trending at the same time on Google News, Google Search, and YouTube and ranks stories based on the relative spike in volume and the absolute volume of searches.

In one embodiment, the pattern recognizer may obtain a pattern definition in a simple format; predict several time steps in future by using Markov models; optimize results based on its predictions; detect transition between patterns; abstract data and extract information to infer higher levels of knowledge; combine higher and lower levels of information to understand about the patient and clinical behaviors; infer from multi-temporal (different time scales) data and associated information; using variable order Markov models, and/or reduce noise over time by employing clustering algorithms, such as k-means clustering.

For example, K vectors are randomly chosen and assigned as a cluster center for applying k-means clustering algorithms. In pattern recognition, the k-means is a method for classifying objects based on the closest training examples in the feature space. k-NN is a type of instance based learning, or lazy learning, where the function is only approximated locally and all computation is differed until classification. The Euclidian distance between different patterns in this vector space may be used to find clusters of patterns. The system may assign a new input vector to its closest cluster center and may move that cluster towards the input vector by a fraction of the Euclidean distance between them.

The system may use knowledge-based components such as a knowledge-based repository (KB). The repository may include clinical information. For example, it may include that "eating salt-rich food causes blood pressure to increase." The information may be stored in a variety of formats based on the type of inference employing them. The knowledge-based repository may act as a repository for some or all of the referenced knowledge. For example, it can include reference values for certain consents and variables used for inference. Accordingly, one or more layers (e.g. a hierarchical pattern processing layer or Pattern Engine) may subscribe to information from the knowledge-based repository. For example, one or more of the services may query the knowledge-based repository when making an inference.

In one embodiment, the knowledge-based repository may aggregate relevant clinical and/or behavioral knowledge from one or more sources. In an embodiment, one or more clinical and/or behavioral experts may manually specify the required knowledge. In another embodiment, an ontology-based approach may be used. For example, the knowledge-based repository may leverage the semantic web using techniques, such as statistical relational learning (SRL). SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'Asian male' and 'smartness', they may be connected using the relationship 'asian males are smart'. This relationship may be given a weight (e.g., 0.3). This relationship may vary from time to time (populations trend over years/decades). By leveraging the knowledge in the semantic web (e.g., all references and discussions on the web where 'asian male' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpora of relevant objects and/or textual resources. These techniques may be used to not only to obtain first-order waited formulae for clinical parameters, but also general information. This information may then be used when making inferences.

For example, if the first order logic is 'obesity causes hypertension, there are two objects involved: obesity and hypertension. If data on patients with obesity and as to whether they were diagnosed with diabetes or not is available, then the weights for this relationship may be learnt from the data. This may be extended to non-clinical examples such as person's mood, beliefs etc.

The pattern recognizer may use the temporal dimension of data to learn representations. The pattern recognizer may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of a matrix. In such an embodiment. C may represent a pattern memory matrix. In the pattern memory matrix, each row of C may be a different pattern. These different patterns may be referred to as C-$1$. C-$2$, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the Markov graph continuously to reflect new probability estimates.

The system may also perform context-specific grouping. To achieve this, the system may partition a set of vertices of the Markov graph into a set of temporal groups. Each temporal group may be a subset of that set of vertices of the Markov graph. The partitioning may be performed such that the vertices of the same temporal group are highly likely to follow one another.

The node may use Hierarchical Clustering (HC) to for the temporal groups. The HC algorithm may take a set of pattern labels and their pair-wise similarity measurements as inputs to produce clusters of pattern labels. The system may cluster the pattern labels such that patterns in the same cluster are similar to each other.

In one embodiment, the probability of a transition between two patterns may be used as the similarity between those patterns for the HC algorithm. The similarity metric may be used to cluster medical patterns that are likely to follow one another into the same cluster. The HC algorithm may be configured such that patterns that are unlikely to follow each other fall into different clusters. A cluster of a set of patterns that are likely to follow each other in time may be referred to as a temporal group. The HC algorithm may start with all store patterns and separate clusters and then recursively merge clusters with the greatest similarity. This may be used to obtain a treelike structure (e.g. a dendrogram) with a single cluster (which may contain all patterns) at the top of the tree and the individual patterns at the bottom (e.g. each pattern in its own cluster). The system may achieve the desired clustering for temporal grouping (e.g. somewhere between the bottom and a top of the dendrogram) by defining a suitable criteria. For example, one criterion could be to cut the tree at a level where the size of the largest cluster does not exceed a particular value. The node may have a design perimeter that sets the maximum number of clusters or temporal groups of the node. The desired temporal groups may be achieved by selecting a level of the dendrogram that gives the number of temporal groups closest to and less than the configured maximum number of temporal groups. These temporal groups may be updated as the Markov transition probabilities are updated. These steps may be performed periodically during the learning process. The learning process may be stopped once the temporal groups have sufficiently stabilized.

Once a node has completed its learning process, it may be used for sensing and/or inference. The characteristics of the input to the node in sensing may be identical to those used during learning. For example, objects may move under the field of view of the node and the node may see portions of those objects. The resulting patterns may be used as inputs to the node.

A node used for sensing and/or inference may produce an output for every input pattern. A node may also use a sequence of patents to produce an output. In one embodiment, it can be assumed that the outputs are produced based on instantaneous inputs. Under this assumption, the Markov graph may not be used during the sensing phase. For example, it may be discarded once the temporal groups within the node are completed.

For every input pattern, the node may produce an output factor that indicates the degree of membership of the input pattern and each of its temporal groups. However, the current input pattern may not perfectly match any of the patterns stored in memory. Accordingly, in one embodiment, the closeness of the input pattern to every pattern stored in memory will be determined. For example, let $d_i$ be the distance of the ith stored pattern from the input pattern. The larger this distance is, the smaller the match between the input pattern and the stored pattern becomes. Assuming that the probability that an input pattern matches a stored pattern falls off as a Gaussian function of the Euclidean distance, the probability that the input pattern matches the ith stored pattern can be calculated as being proportional to $e^{-d2i/\alpha}$, where $\alpha$ is a parameter of the node. Calculating this for every stored pattern may give the closeness of the current input pattern to all the vertices of the Markov graph.

Degree of membership of the input pattern in each temporal group may be determined by the maximum of its closeness to each of the vertices within the temporal group. This results in a length equal to the number of temporal groups, with each component of the factor indicating the degree of membership of the input pattern in the corresponding temporal group. This factor may then be used normalize the sum to unity. These normalized memberships may be used as estimates of probability of membership in each temporal group. This normalized degree of membership may also be used as an output of the node. The output may be a histogram giving estimates of probability of membership of the current input pattern and each of the temporal groups of the node.

As data is fed into the pattern recognizer, the transition probabilities for each pattern and pattern-of-patterns may be updated based on the Markov graph. This may be achieved by updating the constructed transition probability matrix. This may be done for each pattern in every category of patterns. Those with higher probabilities may be chosen and placed in a separate column in the database called a prediction list.

Logical relationships among the patterns may be manually defined based on the clinical relevance. This relationship is specified as first-order logic predicates along with probabilities. These probabilities may be called beliefs. In one embodiment, a Bayesian Belief Network (BBN) may be used to make predictions using these beliefs. The BBN may be used to obtain the probability of each occurrence. These logical relationships may also be based on predicates stored the knowledge base.

The pattern recognizer may also perform optimization for the predictions. In one embodiment, this may be accomplished by comparing the predicted probability for a relationship with its actual occurrence. Then, the difference between the two may be calculated. This may be done for p occurrences of the logic and fed into a K-means clustering algorithm to plot the Euclidean distance between the points. A centroid may be obtained by the algorithm, forming the optimal increment to the difference. This increment may then be added to the (p+1)th occurrence. Then, the process may be repeated. This may be done until the pattern recognizer predicts logical relationships up to a specified accuracy threshold. Then, the results may be considered optimal.

When a node is at the first level of the hierarchy, its input may come directly from the data source, or after some preprocessing. The input to a node at a higher-level may be the concatenation of the outputs of the nodes that are directly connected to it from a lower level. Patterns in higher-level nodes may represent particular coincidences of their groups of children. This input may be obtained as a probability distribution function (PDF). From this PDF, the probability that a particular group is active may be calculated as the probability of the pattern that has the maximum likelihood among all the patterns belonging to that group.

Various aspects of the systems and methods for practicing features of the invention may be implemented on one or more computer systems with processors may also execute one or more computer programs to implement various functions. These computer programs may be written in any type of computer program language, including a procedural programming language, object-oriented programming language, macro language, or combination thereof. These computer programs may be stored in storage system. Storage system may hold information on a volatile or non-volatile medium, and may be fixed or removable and may include a tangible computer-readable and -writable non-volatile recording medium, on which signals are stored that define a computer program or information to be used by the program. The recording medium may, for example, be disk memory, flash memory, and/or any other article(s) of manufacture usable to record and store information. Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

It should also be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound-generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer-readable medium (or multiple computer-readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or one or more other non-transitory, tangible computer-readable storage media) encoded with one or more programs that, when executed on one or more computers or other processors, perform methods that implement the various embodiments of the invention discussed above. The computer-readable medium or media may, for example, be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments. Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than that which is illustrated and described, which may include performing some acts simultaneously, even though shown as sequential acts in the illustrative embodiments described herein.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

What is claimed is:

1. A method for recommending health or beauty products for a subject, comprising:
   receiving from a genetic analyzer subject genetic information;
   aggregating genetic information and health data from a patient population;
   learning with a computer to generate at least one computer implemented classifier that predicts matching health treatments based on the genetic information and health data-from a patient population;
   receiving data from sensors that measure lifestyle habits, skin tone, sleeping patterns, stress, activity, pollution and sun exposure, and receiving data and analytics to identify health or beauty trends using search terms and combining data to offer personalized health or beauty advice for the subject; and
   treating the subject with a health or beauty product resulting from the combined data to offer personalized health or beauty advice for the subject.

2. The method of claim 1, comprising providing custom skin care product, perfume, hair care product, anti-aging product, anti-wrinkle product, or makeup product.

3. The method of claim 1, comprising performing supervised or unsupervised learning selected from support vector machine, random forest, nearest neighbor analysis, linear regression, binary decision tree, discriminant analyses, logistic classifier and cluster analysis.

4. The method of claim 1, wherein the generated prediction data comprises the development of metastases.

5. The method of claim 1, comprising processing type of surgical procedure, age, tumor grading, depth of tumor infiltration, occurrence of post-operative complications, or venous invasion.

6. The method of claim 1, wherein the genetic information comprise variables defining the genomic organization of cells and wherein the provided molecular genetic data comprise variables defining the genomic organization of disseminated cells.

7. The method of claim 1, wherein pre-processing the data comprises transformation of the provided data into class-conditional probabilities.

8. The method of claim 1 wherein genetic sequence information comprises sequence or abundance data from one or more genetic loci in cell-free DNA from the individuals.

9. The method of claim 1 comprising capturing product response including genetic information from the subject generated at a second time point.

10. The method of claim 1, comprising correlating the subject levels of profilaggrin alleles present in genome.

11. The method of claim 1 comprising collection ex-vivo sample from an oral cavity, a nasal cavity, an ear cavity, or behind an ear.

12. The method of claim 1, comprising receiving data from a DNA sequencing machine, a spectrophotometer, a Gas chromatography-mass spectrometry (GC-MS) machine, or a gas chromatography-time-of-flight mass spectrometry (GC×GC-TOF MS) machine, comprising generating a report with a description of one or more signs of the one or more areas of health or beauty.

13. The method of claim 12, comprising determining a subject's genetic potential in the one or more areas of health or beauty including collagen formation, sun protection, antioxidant protection, glycation protection or inflammation control, collagen formation properties, sun protection properties, antioxidant protection properties, glycation protection properties and inflammation control properties.

14. The method of claim 1, comprising checking if health profile matches a predetermined risk and determining deficiency in one or more areas of subject health.

15. The method of claim 1, comprising capture facial image or video; capturing a subject gene; processing the gene for markers of interest; retrieving material data and material interaction data for a treatment substance and determining relative interactions between treatment substances; and selecting one of the treatment substances to the subject.

16. A method for cosmetic or health maintenance of a subject, comprising:
    receiving from a genetic analyzer genetic information from the subject;
    implementing a computer implemented classifier that based on genetic sequence data, predicts beauty or health response of the subject;
    receiving a plurality of genetic information and treatment response over a period of time to see if the treatment improves the subject;
    receiving data from sensors that measure lifestyle habits, skin tone, sleeping patterns, stress, activity, pollution and sun exposure, and receiving data and analytics to identify health or beauty trends using search terms on a search engine; and combining data to offer personalized health or beauty advice for the subject; and
    treating the subject with products for the subject based on the plurality of genetic information and treatment response.

17. The method of claim 16, comprising predicting the development of tumors.

18. The method of claim 16, wherein the genetic information is from a DNA sequencing machine, a spectrophotometer, a Gas chromatography-mass spectrometry (GC-MS) machine, or a gas chromatography-time-of-flight mass spectrometry (GC×GC-TOF MS) machine.

19. The method of claim 16, comprising pre-processing DNA information with a transformation of the DNA information into class-conditional probabilities, wherein the classifier is an artificial neural network trained using a Bayesian framework.

* * * * *